US010556921B2

(12) United States Patent
Williams et al.

(10) Patent No.: US 10,556,921 B2
(45) Date of Patent: Feb. 11, 2020

(54) DEHYDROGENATION OF NEAT FORMIC ACID

(71) Applicant: UNIVERSITY OF SOUTHERN CALIFORNIA, Los Angeles, CA (US)

(72) Inventors: Travis J. Williams, Los Angeles, CA (US); Jeff Joseph A. Celaje, Arcadia, CA (US); Zhiyao Lu, Duarte, CA (US)

(73) Assignee: University of Southern California, Los Angeles, CA (US)

( * ) Notice: Subject to any disclaimer, the term of this patent is extended or adjusted under 35 U.S.C. 154(b) by 0 days.

(21) Appl. No.: 16/246,872

(22) Filed: Jan. 14, 2019

(65) Prior Publication Data
US 2019/0218239 A1 Jul. 18, 2019

Related U.S. Application Data

(63) Continuation of application No. 15/517,701, filed as application No. PCT/US2015/054483 on Oct. 7, 2015, now Pat. No. 10,179,798.

(60) Provisional application No. 62/192,423, filed on Jul. 14, 2015, provisional application No. 62/060,753, filed on Oct. 7, 2014.

(51) Int. Cl.
C07F 15/00 (2006.01)
B01J 31/18 (2006.01)
B01J 31/22 (2006.01)
C01B 3/22 (2006.01)

(52) U.S. Cl.
CPC .......... C07F 15/004 (2013.01); B01J 31/181 (2013.01); B01J 31/189 (2013.01); B01J 31/2239 (2013.01); B01J 31/2295 (2013.01); C01B 3/22 (2013.01); C07F 15/0033 (2013.01); B01J 2231/763 (2013.01); B01J 2531/827 (2013.01); C01B 2203/0277 (2013.01); C01B 2203/1064 (2013.01); C01B 2203/1211 (2013.01)

(58) Field of Classification Search
CPC ... C07F 15/004; C07F 15/008; C07F 15/0033
See application file for complete search history.

(56) References Cited

U.S. PATENT DOCUMENTS

2012/0201744 A1   8/2012  Williams et al.
2017/0014817 A1   1/2017  Williams et al.
2017/0305947 A1   10/2017 Williams et al.

FOREIGN PATENT DOCUMENTS

WO    2016/057661    4/2016

OTHER PUBLICATIONS

Joseph (Nature Communications; 7:11308; 2016; pp. 1-6).*
Greenburg (Dalton Transactions; 2014, 43, 15990-15996).*
Boddien A. et al., "Efficient dehydrogenation of formic acid using an iron catalyst," Science, 2011, v. 333, pp. 1733-1736.
Celaje, J.J.A. et al., "A prolific catalyst for dehydrogenation of neat formic acids," Nature Communications 7, Article No. 11308, Published Apr. 14, 2016, pp. 1-6.
Choi, J. et al., "Dehydrogenation and related reactions catalyzed by iridium pincer complexes," Chem. Rev. 2011, v. 111, pp. 1761-1779.
Greenburg, Z.R. et al., "Nickel promoted functionalization of CO2 to anhydrides and ketoacids," Dalton Trans., 2014, 43, pp. 15990-15996.
Gruber, S. et al., "Characterization and Reactivity Studies of Dinuclear Iridium Hydride Complexes Prepared from Iridium Catalysts with N,P and C,N Ligands Under Hydrogenation Conditions," Organometallics 2013, 32, pp. 4702-4711.
Mellone, I. et al., "Formic acid dehydrogenation catalyzed by ruthenium complexes bearing the tripodal ligans triphos and NP3," DaltonTrans. 2013, v. 42, pp. 2495-2501.
Morris, D.J. et al., "Insights into Hydrogen Generation from Formic Acid Using Ruthenium Complexes," Organometallics 2009, 28, pp. 4133-4140.
Perez, J. et al., "Stable metal-organic complexes as anion hosts," Chem. Soc. Rev., 2008, 37, pp. 2658-2667.
Wang, W-H. et al., "Chapter 10. Recent advances in transition metal-catalysed homogeneous hydrogenation of carbon dioxide in aqueous media," Hydrogenation, book edited by Iyad Karame, ISBN 978-953-51-0785-9, Published Oct. 10, 2012, pp. 250-268.

(Continued)

Primary Examiner — Pancham Bakshi
(74) Attorney, Agent, or Firm — Brooks Kushman P.C.

(57) ABSTRACT

A formic acid decomposition catalyst system includes organometallic complexes having formula 1:

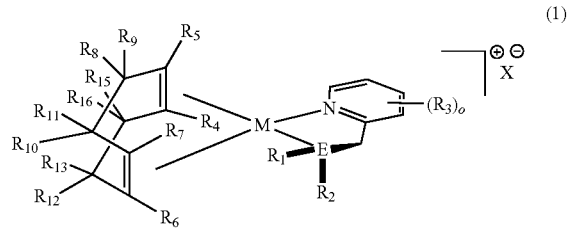

wherein:
M is a transition metal;
E is P, N, or C (as in imidazolium carbene);
$R_1$, $R_2$ are independently $C_{1-6}$ alkyl groups;
o is 1, 2, 3, or 4;
$R_3$ are independently hydrogen, $C_{1-6}$ alkyl groups, $OR_{14}$, $NO_2$, halogen;
$R_4$, $R_5$, $R_6$, $R_7$, $R_8$, $R_9$, $R_{10}$, $R_{11}$, $R_{12}$, $R_{13}$, $R_{15}$, $R_{16}$ are independently hydrogen or $C_{1-6}$ alkyl groups;
$R_{14}$ is a $C_{1-6}$ alkyl group; and
$X^-$ is a negatively charge counter ion.

15 Claims, 21 Drawing Sheets

(56) References Cited

OTHER PUBLICATIONS

International Search Report dated Jan. 4, 2016 for PCT Appn. No. PCT/US2015/054483 filed Oct. 7, 2015, 6 pgs.
Notice of Allowance dated Feb. 7, 2017, U.S. Appl. No. 15/210,350, 7 pgs.
Non-final Office Action dated Sep. 26, 2016, U.S. Appl. No. 15/210,350, 8 pgs.
Non-final Office Action dated Dec. 5, 2017, U.S. Appl. No. 15/210,350, 21 pgs.
Non-final Office Action dated May 4, 2018, U.S. Appl. No. 15/517,701, 22 pgs.

* cited by examiner

DEHYDROGENATION OF NEAT FORMIC ACID

CROSS-REFERENCE TO RELATED APPLICATIONS

This application is a continuation of U.S. patent application Ser. No. 15/517,701 filed Apr. 7, 2017, now U.S. Pat. No. 10,179,798 issued Jan. 15, 2019, which is the U.S. National Phase of PCT Appln. No. PCT/US2015/054483 filed Oct. 7, 2015, which claims the benefit of U.S. provisional application Ser. No. 62/060,753 filed Oct. 7, 2014 and 62/192,423 filed Jul. 14, 2015, the disclosures of which are hereby incorporated in their entirety by reference herein.

STATEMENT REGARDING FEDERALLY SPONSORED RESEARCH OR DEVELOPMENT

The invention was made with Government support under grant No. CHE-1054910 awarded by the National Science Foundation. The Government has certain rights to the invention.

TECHNICAL FIELD

In at least one aspect, the present invention is related to organometallic complexes that catalyze the decomposition of formic acid.

BACKGROUND

Ongoing research in the area of sustainable solutions to alleviate petrochemical dependence includes solar fuels, the effort to synthesize liquid fuel materials based on harnessed solar energy. This work is important, because it enables us to provide commodity chemicals and energy carriers without reliance on petroleum products. Many of these strategies involve electrocatalytic (or photocatalytic) cleavage of water to form hydrogen and oxygen. The reducing equivalent, $H_2$, is thus an energy carrier because it can be re-oxidized, either by combustion to give heat or catalytically in a fuel cell to give electricity. There is a disabling problem with large-scale utilization of hydrogen as a fuel, since it is a gas under ambient conditions, thus limiting its volume-energy density (0.013 MJ $L^{-1}$). As a result, physical-based hydrogen storage technologies (compression, cryogenic liquefaction, adsorption) involve low capacity, high costs, or safety issues. Therefore, the discovery of highly weight-efficient strategies for on-demand hydrogen release from hydrogen-rich liquids has potential value toward enabling hydrogen (with an appropriate $H_2$ oxidation fuel cell) as a renewable fuel for light vehicles. Formic acid ($HCO_2H$, FA, 7.5 MJ $L^{-1}$) is a hydrogen carrier, owing to its ability to release hydrogen under mild conditions with only $CO_2$ as a by-product, which can then be recycled, in principle, to give a carbon-neutral fuel cycle.

To date, many efficient homogeneous and heterogeneous catalysts for FA dehydrogenation have been developed. Heterogeneous catalysts have advantages of separability and reusability, while homogeneous catalysts are generally more efficient, the latter exhibiting the best turnover number and turnover frequency. Moreover, homogeneous catalysts generally are more selective, producing less carbon monoxide, a common byproduct of FA dehydrogenation. This is essential, because CO is a fuel cell catalyst poison. Still, no known system is stable and reactive through multiple uses, air and water tolerant, selective against CO formation, and functions in neat formic acid liquid. Each of these is critical to achieving a usable hydrogen generation system based on formic acid. Herein we report a novel iridium-based catalytic system that meets all of these criteria.

Accordingly, there is a need for new catalyst systems for reducing formic acid and related compounds.

SUMMARY

The present invention solves one or more problems of the prior art by providing in at least one embodiment, a formic acid decomposition catalyst system. The catalyst system includes organometallic complexes having general formula A:

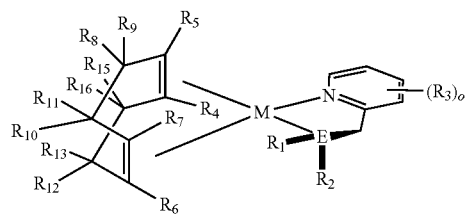

(A)

wherein:
M is a transition metal;
E is P, N, or C (as in imidazolium carbene);
$R_1$, $R_2$ are independently $C_{1-6}$ alkyl groups;
o is 1, 2, 3, or 4;
$R_3$ are independently hydrogen, $C_{1-6}$ alkyl groups, $OR_{14}$, $NO_2$, halogen;
$R_4$, $R_5$, $R_6$, $R_7$, $R_8$, $R_9$, $R_{10}$, $R_{11}$, $R_{12}$, $R_{13}$, $R_{15}$, $R_{16}$ are independently hydrogen or $C_{1-6}$ alkyl groups;
$R_{14}$ is a $C_{1-6}$ alkyl group; and
$X^-$ is a negatively charge counter ion.

In another embodiment, an organometallic complex having formula B is provided:

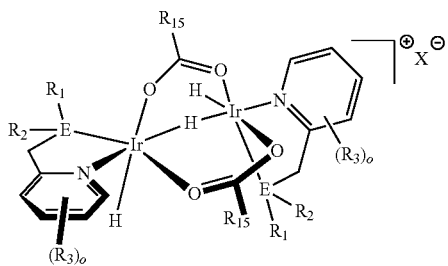

(B)

wherein:
M is a transition metal;
E is P, N, or C (as in imidazolium carbene);
$R_1$, $R_2$ are each independently $C_{1-6}$ alkyl groups;
$R_3$ are each independently hydrogen, $C_{1-6}$ alkyl groups, $OR_{14}$, $NO_2$, halogen;
o is 1, 2, 3, or 4;
$R_{14}$ is hydrogen or a $C_{1-6}$ alkyl group;
$R_{15}$ is hydrogen or a $C_{1-6}$ alkyl group; and
$X^-$ is a negatively charge counter ion. Complexes having general formula B are prepared by dimerizing complexes having general formula A.

In another embodiment, a method of dehydrogenating formic acid is provided. The method includes a step of contacting the catalyst system including the organometallic complex having formula A and/or B with formic acid in the presence of a base. Advantageously, this step is performed substantially free of solvents other than formic acid. Molecular hydrogen is then collected from the reaction of formic acid with the complex having general formula A and/or B.

Embodiments provide a new catalytic system for the repeated conversion of formic acid to $CO_2$ and hydrogen. This has translation potential because it is the first known system to operate in neat formic acid, thus enabling far greater weight content of $H_2$ release than any other known catalyst for FA dehydrogenation. Further, it is by far the highest turnover system, because, in part, it can be re-used directly with formic acid substrate that is not rigorously purified or dried. The catalyst can be re-used without regeneration through multiple cycles. While many solutions are known for formic acid dehydrogenation, none has both the mild conditions and high selectivity while being tolerant of high formic acid concentrations with low base loading. Together, these findings make the catalyst system of the present invention capable of generating the highest wt % of $H_2$ from a formic acid reactor.

BRIEF DESCRIPTION OF THE DRAWINGS

FIG. 2A shows catalyst initiation for catalyst 3a;

DETAILED DESCRIPTION

Figure 1:
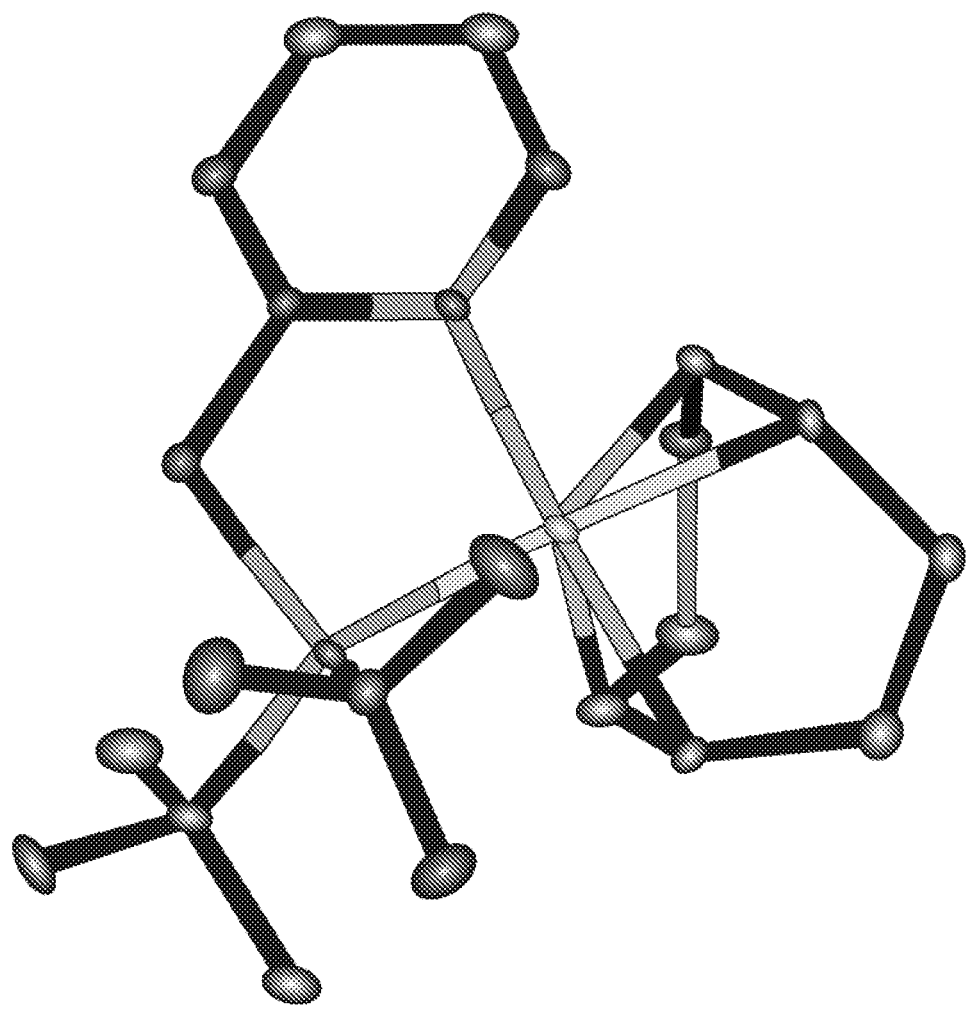
FIG. 1 provides an ORTEP diagram of iridium complex 1 with ellipsoids drawn at the 50% probability level.

Reference will now be made in detail to presently preferred compositions, embodiments and methods of the present invention, which constitute the best modes of practicing the invention presently known to the inventors. The Figures are not necessarily to scale. However, it is to be understood that the disclosed embodiments are merely exemplary of the invention that may be embodied in various and alternative forms. Therefore, specific details disclosed herein are not to be interpreted as limiting, but merely as a representative basis for any aspect of the invention and/or as a representative basis for teaching one skilled in the art to variously employ the present invention.

Except in the examples, or where otherwise expressly indicated, all numerical quantities in this description indicating amounts of material or conditions of reaction and/or use are to be understood as modified by the word "about" in describing the broadest scope of the invention. Practice within the numerical limits stated is generally preferred. Also, unless expressly stated to the contrary: all R groups include H and $C_{1-6}$ alkyl groups; X groups include halides; subscripts for the number of a group is 0 or 1 or 2 or 3 or 4; percent, "parts of," and ratio values are by weight; the description of a group or class of materials as suitable or preferred for a given purpose in connection with the invention implies that mixtures of any two or more of the members of the group or class are equally suitable or preferred; description of constituents in chemical terms refers to the constituents at the time of addition to any combination specified in the description, and does not necessarily preclude chemical interactions among the constituents of a mixture once mixed; the first definition of an acronym or other abbreviation applies to all subsequent uses herein of the same abbreviation and applies mutatis mutandis to normal grammatical variations of the initially-defined abbreviation; and, unless expressly stated to the contrary, measurement of a property is determined by the same technique as previously or later referenced for the same property.

It is also to be understood that this invention is not limited to the specific embodiments and methods described below, as specific components and/or conditions may, of course, vary. Furthermore, the terminology used herein is used only for the purpose of describing particular embodiments of the present invention and is not intended to be limiting in any way.

It must also be noted that, as used in the specification and the appended claims, the singular form "a," "an," and "the" comprise plural referents unless the context clearly indicates otherwise. For example, reference to a component in the singular is intended to comprise a plurality of components.

Abbreviations

"FA" is formic acid;
"OTf" is trifluoromethanesulfonate.

In an embodiment, a formic acid dehydrogenation catalyst system is provided. The catalyst system includes an organometallic complex having formula A is provided:

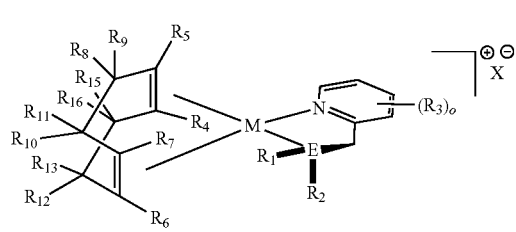

(A)

wherein:
M is a transition metal;
E is P, N, or C (as in imidazolium carbene);
$R_1$, $R_2$ are each independently $C_{1-6}$ alkyl groups;
$R_3$ are each independently hydrogen, $C_{1-6}$ alkyl groups, $OR_{14}$, $NO_2$, or halogen;
o is 1, 2, 3, or 4;
$R_4$, $R_5$, $R_6$, $R_7$, $R_8$, $R_9$, $R_{10}$, $R_{11}$, $R_{12}$, $R_{13}$, $R_{15}$, $R_{16}$ are each independently hydrogen or $C_{1-6}$ alkyl groups;
$R_{14}$ is hydrogen or $C_{1-6}$ alkyl group; and
$X^-$ is a negatively charge counter ion such as halide or trifluoromethanesulfonate (OTf). Typically, the catalyst system also includes a base as a co-catalyst.

In a variation M is a metal selected from the group consisting of beryllium, magnesium, aluminum, scandium, titanium, vanadium, chromium, manganese, iron, cobalt, nickel, copper, zinc, gallium, germanium, yttrium, zirconium, niobium, molybdenum, technetium, ruthenium, rhodium, palladium, silver, cadmium, indium, tin, antimony, lanthanum, cerium, praseodymium, neodymium, promethium, samarium, europium, gadolinium, terbium, dysprosium, holmium, erbium, thalium, ytterbium, lutetium, hafnium, tantalum, tungsten, rhenium, osmium, iridium, gold, platinum, thallium, lead, bismuth, polonium, thorium, protactinium, uranium, neptunium, and plutonium. In a refinement, M is a transition metal selected from the group consisting of ruthenium, rhodium, iridium, and iron. In another refinement, M is ruthenium.

In another variation, $R_1$, $R_2$ are methyl, ethyl, butyl, n-propyl, isopropyl, n-butyl, sec-butyl, t-butyl. In a refinement, $R_1$, $R_2$ are t-butyl.

In still another variation, the $R_3$ are each independently selected from the group consisting of hydrogen, methyl, ethyl, butyl, n-propyl, isopropyl, n-butyl, sec-butyl, t-butyl. In a refinement, the $R_3$ are hydrogen.

In yet another variation, $R_4$, $R_5$, $R_6$, $R_7$, $R_8$, $R_9$, $R_{10}$, $R_{11}$, $R_{12}$, $R_{13}$, are each independently methyl, ethyl, butyl, n-propyl, isopropyl, n-butyl, sec-butyl, t-butyl. In a refinement, the $R_4$, $R_5$, $R_6$, $R_7$, $R_8$, $R_9$, $R_{10}$, $R_{11}$, $R_{12}$, $R_{13}$ are each independently hydrogen.

In an refinement, the orgranometallic complex is described by formula 1:

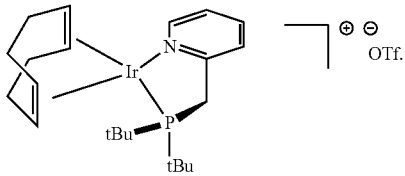

(1)

Iridium complex 1 is an efficient and selective homogeneous catalyst for decomposition of neat formic acid into $H_2$ and $CO_2$.

In another embodiment, a formic acid dehydrogenation catalyst system is provided. The catalyst system includes an organometallic complex having formula B is provided:

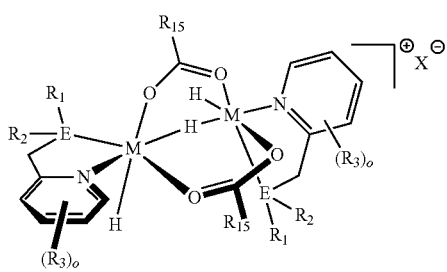

(B)

wherein M, $R_1$, $R_2$, $R_3$, o, and $X^-$ are as set forth above including all variations and refinements. $R_{15}$ is hydrogen or a $C_{1-6}$ alkyl group. E is P, N, or C (as in imidazolium carbene). In a variation, $R_{15}$ is selected from the group consisting of hydrogen, methyl, ethyl, butyl, n-propyl, isopropyl, n-butyl, sec-butyl, t-butyl. The complexes having general formula B are formed by dimerizing complexes having general formula A. This dimerization can occur in the presence of formic acid, formate, or combinations thereof. In a particular refinement, $R_{15}$ is hydrogen or methyl. In a further refinement, $R_3$ is hydrogen and is $R_1$, $R_2$ is t-butyl.

In another embodiment, a method of dehydrogenating formic acid is provided. The method includes a step of contacting the organometallic complex having general formula A and/or B and in particular, formula 1, with formic acid in the presence of a base. Advantageously, this step is performed substantially free of solvents other than formic acid (i.e., less than 1 weight percent of the combined weight of catalyst and formic acid). In a refinement, this step is performed with solvents other than formic acid in an amount less than, in increasing order of preference, 20 weight percent, 10 weight percent, 5 weight percent, 2 weight percent, 1 weight percent, 0.1 weight percent, or 0.1 weight percent of the combined weight of the formic acid and complex having formula 1. Molecular hydrogen is then collected from the reaction of formic acid with the complex 1.

The reaction using the organometallic complex having general formula A, and in particular, formula 1 requires base as co-catalyst. The rate of dehydrogenation is approximately the same when 5% of $CaCO_3$, KOH, NaOH, $NaO_2CH$ (sodium formate), and LiOH are used. The reaction proceeds about twice as fast when 5% of $Na_2CO_3$ and $K_2CO_3$ are used. Any of these bases are rapidly converted to the corresponding metal formate, which comprises the bulk of the catalytic material and gives it its white color. Because this is part of the catalyst, it does not accumulate over time.

The following examples illustrate the various embodiments of the present invention. Those skilled in the art will recognize many variations that are within the spirit of the present invention and scope of the claims.

Reactivity in Formic Acid Dehydrogenation.

Complex 1, which is easily prepared from known materials (FIG. 1A), decomposes formic acid (500 μL, 12.7 mmol) with NaO$_2$CH co-catalyst (5 mol %) at 50 ppm loading and 90° C., resulting in the production of 386 mL of gas (62% conversion; TON=12530) after 13 h. The rate of the reaction is constant through ca. 20% of conversion before it accelerates as FA disappears. At the end of the reaction, a pale orange solid (the catalyst system: an iridium complex and sodium formate), remains at the bottom of the reaction vessel. Recharging the reaction flask with formic acid and reheating to 90° C. results in continued H$_2$ production without any catalyst regeneration.

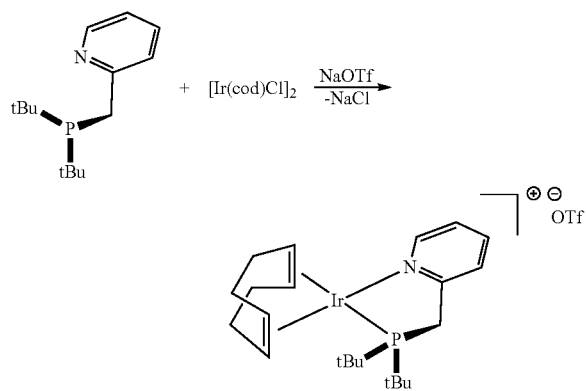

The reaction requires base as co-catalyst, but the source of the base is not specific: the reaction rates are similar when 5 mol % NaO$_2$CH, KO$_2$CH, KOH, NaOH, LiOH, or nBu$_4$NOH or 2.5 mol % of Na$_2$CO$_3$ or K$_2$CO$_3$ is used. Any of these are converted rapidly to the corresponding formate, which comprises the bulk of the catalytic material and gives it its pale color. Moreover, water does not affect the rate of dehydrogenation significantly—the double logarithmic plot of water concentration versus rate of FA dehydrogenation yields a slope of 0.11(5).

The catalysts are air stable. Although dehydrogenation is slower when the catalysts are prepared in air, the system remains active, even when the solution is allowed to sit on the bench top for two weeks before dehydrogenation rates are measured. Under these conditions, the catalysts can be re-loaded in an air atmosphere and re-used repeatedly. For example, a reaction flask containing iridium 1 (6.1 mg, 8.9 μmol) and NaO$_2$CH (185 mg, 2.72 mmol) was charged with formic acid through 50 cycles. In this experiment 28.85 L of gas were produced from 25 mL of formic acid, corresponding to a turnover number of 66,403 and 89% conversion. Over the course of 50 loadings, we measured the initial rates and maximum turnover frequencies during certain runs (Table 1). Interestingly, these increased over the course of ten cycles before slowing over time.

TABLE 1

Catalyst performance over iterative uses.

| Entry | Loading | Initial Rate (μmol s$^{-1}$) | Maximum Turnover Frequency (h$^{-1}$) |
|---|---|---|---|
| 1 | 1$^{st}$ | 0.52 | 1378 |
| 2 | 10$^{th}$ | 2.35 | 3032 |
| 3 | 20$^{th}$ | 2.77 | 2756 |
| 4 | 30$^{th}$ | 2.82 | 2618 |
| 5 | 40$^{th}$ | 2.51 | 2205 |
| 6 | 50$^{th}$ | 1.46 | 1519 |

The iridium catalyst delivers very high turnover numbers at low loading with repeated re-use. For example, we prepared in the drybox a reaction flask containing 1 (90 μg, 0.13 μmol) and NaO$_2$CH (184 mg, 2.65 mmol) and repeatedly charged it with formic acid, which was decomposed until a pale yellow solid remained at the bottom of the flask. After 40 cycles over a period of four months, 13.71 L of gas were produced, which corresponds to a turnover number of 2.16 million. Although unoptimized, this is the best turnover number for a formic acid dehydrogenation catalyst known to date to our knowledge. Under these conditions, the maximum TOF was measured to be 3.7 s$^{-1}$.

The reaction is operationally simple. The catalytic materials are weighed out in a reactor, which is attached to a vent line for the gaseous products. Liquid FA is added, and the reaction is initiated by heating. Upon completion, the catalyst system remains as a pale-colored precipitate at the bottom of the vessel for re-use.

To be useful in fuel cells, FA decomposition must be selective for H$_2$ and CO$_2$ over H$_2$O and CO, because CO is a poison for PEM fuel cell catalysts such as platinum. The composition of gas produced from our conditions was determined by gas chromatography, which showed only H$_2$ and CO$_2$ (1:1 ratio) and no detectable CO (<1 part per thousand).

The active catalyst is found to be homogeneous on the basis of physical appearance, clean kinetics, tolerance of liquid mercury, and proportional inhibition by phenanthroline. Accordingly, the system exhibits the reactivity and selectivity advantages of homogeneous catalysis. Nonetheless, because the catalytic materials are deposited cleanly in the reactor at the end of the reaction, the system enjoys many of the catalyst separability and reusability benefits of heterogeneous conditions.

Mechanistic Studies.

Figure 2A:
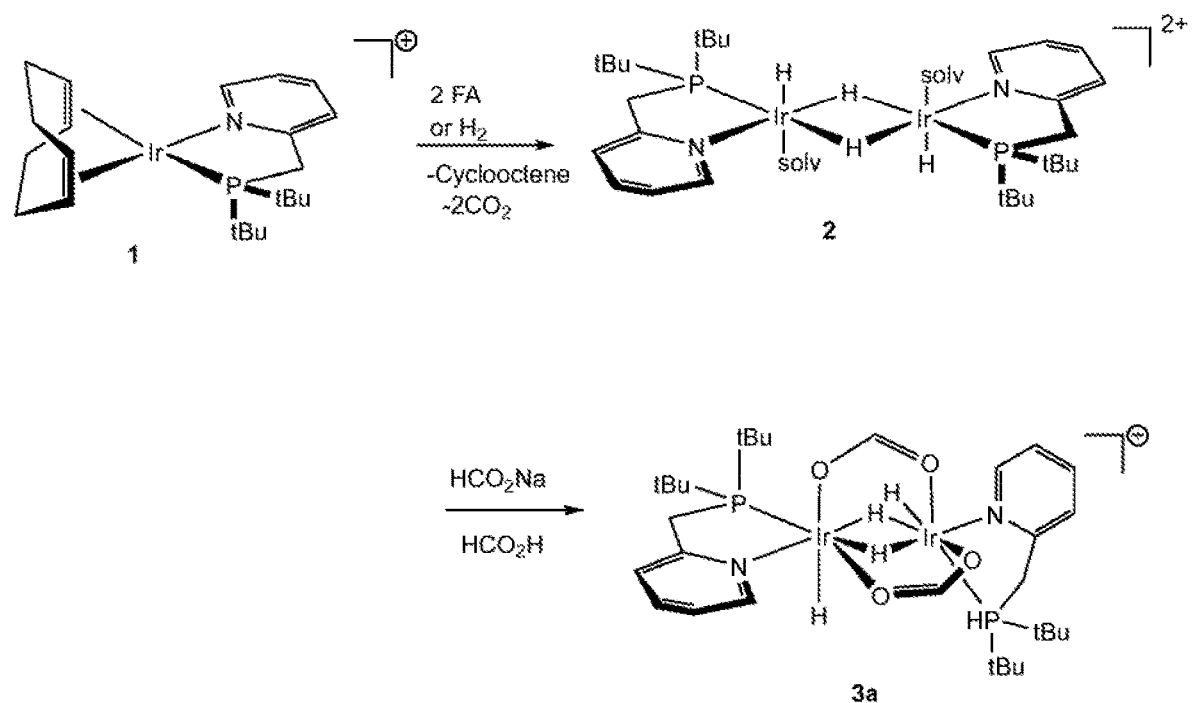
Figure 2B:
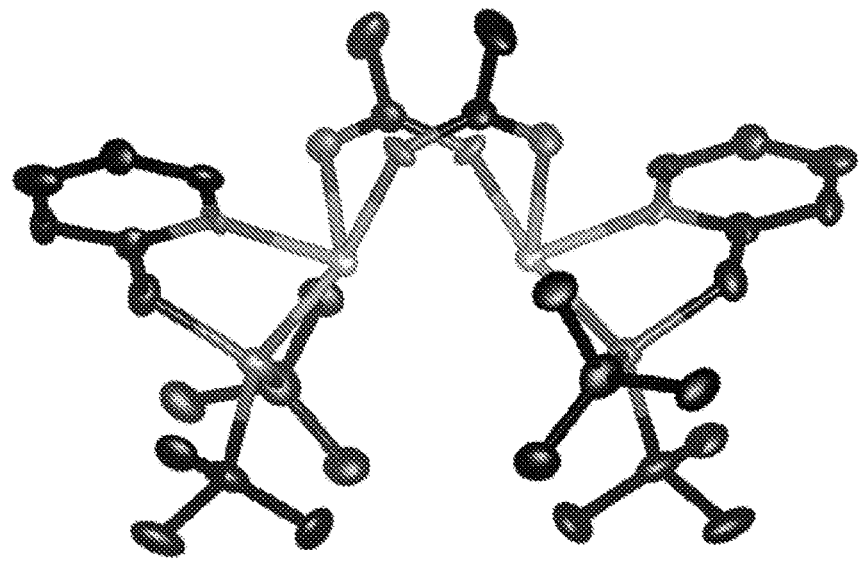
FIG. 2B provides an ORTEP diagram of active catalyst homologue $3b=\{[(tBu_2PCH_2(2-py))Ir(H)]_2(\mu^2-H)(\mu^2-\kappa,\kappa'-O_2CCH_3)_2\}^+$ with hydrogen atoms omitted and ellipsoids drawn at the 50% probability level.
Figure 3:
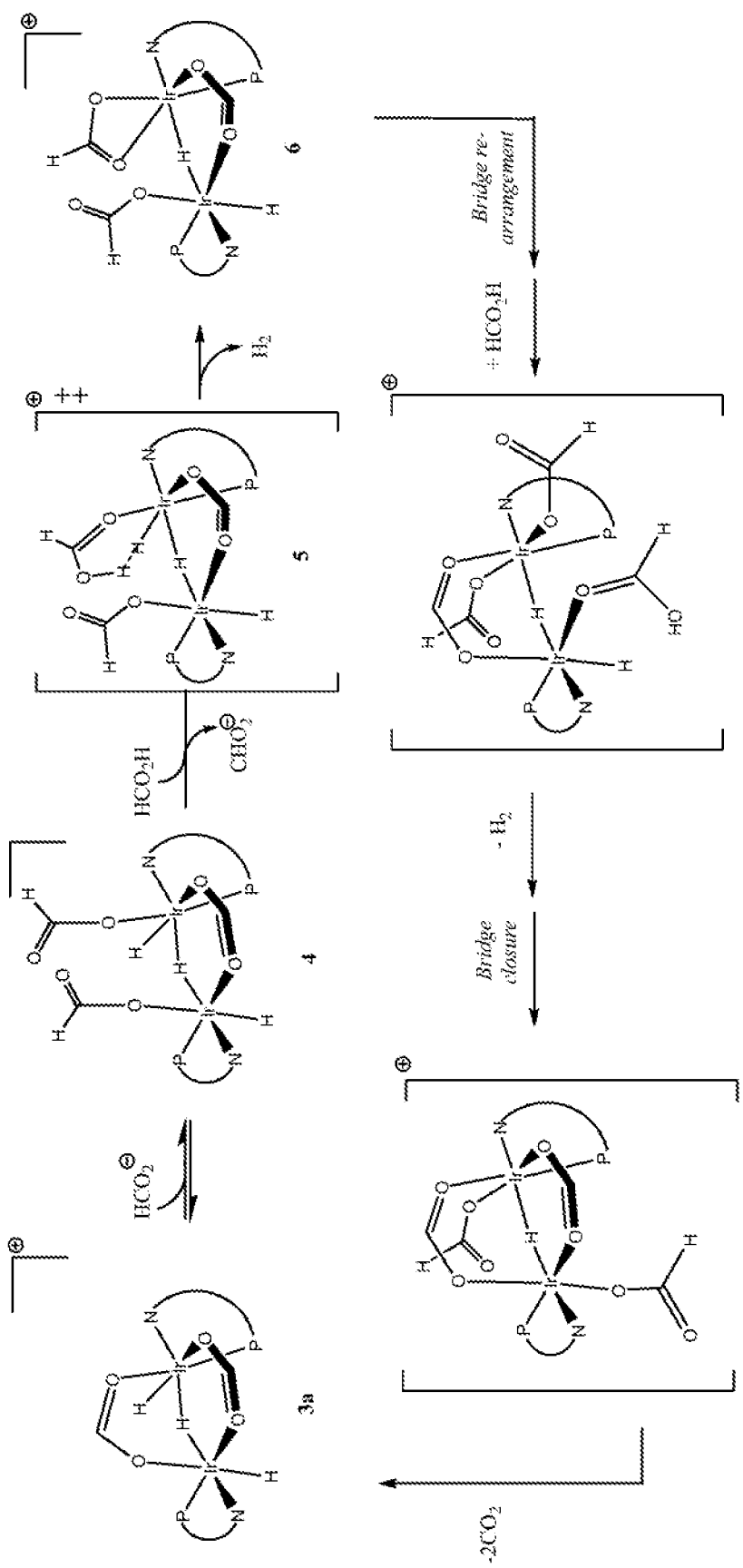
FIG. 3 provides a possible catalytic mechanism for reactions of compounds having general formula A.

Equally remarkable as the reactivity of this new catalytic system is the unique, two metal mechanism through which it operates. Three approaches were used to gain insight into this mechanism: stoichiometric model reactions, reaction kinetics, and isotope labeling studies. FIG. 2 presents a sketch of a possible mechanism for our system.

Species 1 is a catalyst precursor from which an active catalyst is generated. To determine the nature of this active species, we conducted stoichiometric reactions of 1 (FIG. 1A). Species 1 loses its cyclooctadiene ligand as cyclooctene in a solution of either H$_2$ or buffered formic acid and dimerizes to form 2. Complex 2 has analogy to {[(P—N)Ir(CH$_2$Cl$_2$)(H)]$_2$(μ$^2$-H)$_2$}$^{2+}$ characterized by Pfaltz (Gruber, S., Neuburger, M., & Pfaltz, A. Characterization and reactivity studies of dinuclear iridium hydride complexes prepared from iridium catalysts with N,P and C,N ligands under hydrogenation conditions. *Organometallics* 32, 4702-4711 (2013)) (P—N=SimplePHOX). In buffered formic acid conditions, 2 is then converted to a formate-bridged species 3a. While this species is observable by NMR, it is not amenable to isolation in our hands. By contrast, its acetate homologue (3b) yielded to crystallization, which enabled determination of its structure. Species 3a is relevant in catalysis: we observe it by NMR as the minor form of the working catalyst. We see a second, major resting species by NMR, which has a spectrum consistent with structure 4, featuring three differentiated metal hydride groups.

Kinetic isotope effect data indicate that both the C—H and O—H groups of formic acid are involved in (or before) the rate-determining transition state. Table 2 (left) summarizes the reaction rates for four selectively labeled formic acid isotopologues. The combined isotope effect ($k_{CHOH}/k_{COD}$=6.5(2)) is comparable to the product of the average separate C—H and O—H isotope effects (6.5(4)). This is consistent with a mechanism in which bonds to proton and hydride are transformed in a single kinetically relevant step. Hydrogen loss from 4 involves protonation of an iridium hydride (which comes from FA's C—H group) by a formic acid group. Further, we observe that in a sample of formic acid-(O)-$d_1$, NMR reveals HD as the catalytic product. This indicates that there is separation of proton and hydride groups throughout the mechanism and refutes the possibility of an iridium dihydride species in the mechanism, because such a species would be likely to enable proton/hydride scrambling via reversible reductive elimination of dihydrogen. This observation also shows that the reaction is irreversible at ambient pressure, so we assign the isotope effects as kinetic.

formate bridge in dimer 3a. The rate law also has [Ir] first order, which indicates a dimeric iridium species that does not dissociate once formed. Inverse order in [FA] implies inhibition, but the origins of this inhibition are unclear. Acid is known to favor closure of carboxylate bridges in ruthenium species similar to those of the present invention (Morris, D. J., Clarkson, G. J., & Wills, M. Insights into hydrogen generation from formic acid using ruthenium complexes. *Organometallics* 28, 4133-4140 (2009)), which enables several opportunities for formic acid inhibition in our mechanism. Moreover, formic acid has potential roles in the conversion of 4 and as solvent. We are currently studying this complex system of interactions.

Methods

All air and water sensitive procedures were carried out either in a Vacuum Atmosphere glove box under nitrogen (2-10 ppm $O_2$ for all manipulations) or using standard Schlenk techniques under nitrogen. Dichloromethane-$d_2$, acetonitrile-$d_3$, methanol-$d_4$, water-$d_2$, formic acid-$d_1$ (C-D), and formic acid-$d_1$ (O-D) NMR solvents and reagents were purchased from Cambridge Isotopes Laboratories. Formic acid-$d_2$ was purchased from SynQuest Laboratories. Dichloromethane, ethyl ether, and hexanes were purchased from VWR and dried in a J. C. Meyer solvent purification system with alumina/copper(II) oxide columns; chloro(1,5-cyclooctadiene)iridium(I) dimer (Strem), sodium trifluoromethanesulfonate (Sigma-Aldrich), and formic acid (Sigma-Aldrich)

TABLE 2

Reaction Kinetics.

| Compound | $k_{rel}$ | KIE (observed) | | | Neat[a] | Solution[a,d] |
|---|---|---|---|---|---|---|
| $HCO_2H$ | 6.5(2) | $k_{CHOH}/k_{CHOD}$ | 1.8(3) | [Ir] | 0.95(3)[b] | 0.96(4)[e] |
| $HCO_2D$ | 3.6(2) | $k_{CDOH}/k_{CDOD}$ | 1.65(3) | [base] | 0.64(5)[c] | 0.44(2)[f] |
| $DCO_2H$ | 1.6(2) | $k_{CHOH}/k_{CDOH}$ | 3.9(2) | [FA] | — | −0.94(9)[g] |
| $DCO_2D$ | 1.00(2) | $k_{CHOD}/k_{CDOD}$ | 3.6(2) | | | |
| | | $k_{CHOH}/k_{CDOD}$ | 6.5(2) | | | |

Left: isotope effect data. Conditions are 50 ppm 1, 5 mol % base, 86° C. Right: reaction order.
[a]Data were collected at 86° C. as an average of two runs.
[b]Data collected using 0.63M [$NaO_2CH$] (2.5 mol %) and [Ir] ranging among 0.63, 1.86, 2.59, 3.25, and 4.41 mM.
[c]Data were collected using 0.66 mM [Ir], and [$NaO_2CH$] ranging among 0.26, 0.53, 1.06, 1.59, 2.11, and 2.65M.
[d]Tetraglyme was used as solvent. Base was delivered as (n-Bu)$_4$NOH to generate soluble (n-Bu)$_4$N($O_2$CH).
[e]Data were collected using 13.2 mM [(n-Bu)$_4$N($O_2$CH)] (5 mol %) and [Ir] concentration ranging among 0.066, 0.13, 0.20, 0.26, and 0.33 mM.
[f]Data were collected using 0.066 mM [Ir] and [(n-Bu)$_4$N($O_2$CH)] ranging among 13.2, 26.4, 39.6, 52.8, and 66.0 mM.
[g]Data were collected using 0.026 [Ir], 13.2 mM [(n-Bu)$_4$N($O_2$CH)], and [FA] ranging among 265, 331, 398, 530 and 662 mM.

Eyring analysis reveals activation parameters of $\Delta H^{\ddagger}$=+29.0(3) kcal mol$^{-1}$ and $\Delta S^{\ddagger}$=+16(1) eu. This strongly favorable entropy of activation is consistent with the release of at least one gaseous product in the rate determining transition state. We expect that this is $H_2$ release in the conversion of 4 to 6 because of the strong isotope effects.

The observed rate law for FA dehydrogenation has rate~[Ir]$^1$[base]$^{0.5}$[FA]$^{-1}$, which is based on the slopes of double logarithmic plots recorded both in neat formic acid and dilute in tetraglyme solution (Table 2, left). This rate law requires that two sites of the catalyst are activated by a single equivalent of formate, thus causing half order dependence on base. After the first equivalent of $H_2$ is lost in the conversion of 4 to 6, a second equivalent forms from the iridium hydride on the complementary metal center. It appears that the latter is more rapid than the former, and that the single equivalent of formate enables both by opening a were purchased and used as received; 2-(($d_1$-t-butylphosphino)methyl)pyridine was synthesized using a literature procedure (24).

NMR spectra were recorded on a Varian VNMRS 500 or VNMRS 600 spectrometer. All chemical shifts are reported in units of ppm and referenced to the residual $^1$H or $^{13}$C solvent peak and line-listed according to (s) singlet, (bs) broad singlet, (d) doublet, (t) triplet, (dd) double doublet, etc. $^{13}$C spectra are delimited by carbon peaks, not carbon count. $^{31}$P chemical shifts are referenced to an 85% phosphoric acid external standard. Air-sensitive NMR spectra were taken in 8" J-Young tubes (Wilmad or Norell) with Teflon valve plugs. MALDI mass spectra were obtained on an Applied Biosystems Voyager spectrometer using the evaporated drop method on a coated 96 well plate. The matrix was 2,5-dihydroxybenzoic acid. In a standard preparation, ca. 1 mg analyte and ca. 10 mg matrix was dissolved in methanol and spotted on the plate with a glass capillary. Infrared spectra were recorded on Bruker OPUS FTIR spectrometer. X-ray crystallography data were obtained on a Bruker APEX DUO single-crystal diffractometer equipped with an APEX2 CCD detector, Mo fine-focus and Cu micro-focus X-ray sources. Gas chromatography data were obtained on a Thermo gas chromatograph (Supelco Carboxen®-1010 plot, 30 m×0.53 mm) equipped with a TCD detector (detection limit: 0.099 v/v %) and with a Jasco FT-IR instrument. Elemental analysis data were obtained on a Thermo Flash 2000 CHNS Elemental Analyzer.

Dehydrogenation Procedures

The dehydrogenation of formic acid can generally be performed by preparing a stock solution of the catalysts. In the drybox, formate and the iridium precatalyst are dissolved in either formic acid or tetraglyme solvent. The resulting orange solution slowly turns pale yellow over the course of ca. 1 hour. The solution is allowed to sit for several hours or overnight before the catalyst is used for dehydrogenation reactions.

Method 1: Reactions Followed to Completion

In the drybox, a 0.5 mL aliquot of a stock solution is transferred into a 5 mL high pressure reaction flask possessing a side arm and a large bore plug valve. The flask is then taken out of the drybox and connected to a vent line leading to a gas buret filled with oil (a eudiometer). To follow the reaction to completion, a 1000 mL gas buret is used. The reaction flask is heated to 90° C. in an oil bath for ca. 15 minutes before opening the valve. The volume of gas produced over time is recorded.

Method 2: Accurate Measurements of Initial Rates

In the dry box, a 0.5 mL aliquot of a stock solution is transferred into a 5 mL reaction flask possessing a large bore plug valve and a side arm. This flask is taken out of the drybox and the sidearm is connected to a three-way valve, which is connected to a nitrogen line and a 50.00 mL gas buret. The tubing and gas buret are purged with nitrogen for ca. 15 minutes. The reaction flask is then heated in an oil bath to 86° C. Because the oil bath temperature increases after initial heating, the reaction is heated for ca. 15 min before readings are taken to allow the temperature to equilibrate. The volume of gas formed over time was then recorded. The initial rate of formic acid decomposition (average of two runs) was obtained from a plot of moles of formic acid decomposed versus time (20 data points were obtained in each experiment).

Synthesis Procedures and Characterization Data

Complex 1

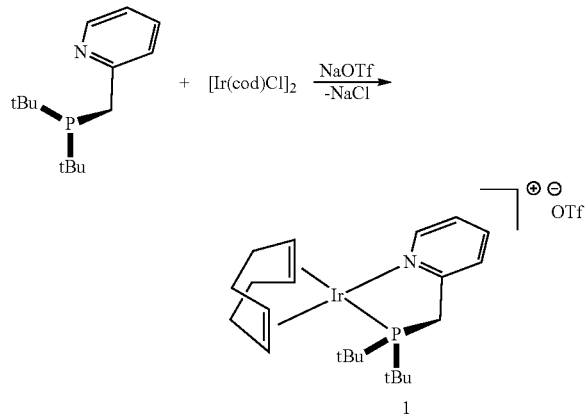

In the drybox under nitrogen, 2-((di-t-butylphosphino)methyl)pyridine (105.3 mg, 0.44 mmol)[1] was dissolved in a dry vial in 5 mL of dry dichloromethane. In another vial containing a Teflon stir bar, chloro(1,5-cyclooctadiene)Iridium(I) dimer (149.0 mg, 0.22 mmol) and sodium trifluoromethanesulfonate (130 mg, 0.75 mmol) were suspended in 10 mL of dry dichloromethane. The suspension was stirred vigorously and then the phosphinopyridine solution was added slowly dropwise. The phosphinopyridine vial was rinsed with 5 mL of dichloromethane and added to the stirred suspension. After stirring for 1 hour, the solution was filtered to remove the sodium chloride byproduct and the excess sodium triflate. The solvent was evaporated under reduced pressure to yield an orange glassy solid. A 5:1 mixture of dry hexanes/ethyl ether (10 mL) was added to the residue, and then triturated by sonication. The hexane was decanted and the residue washed with an additional 10 mL of hexanes/ethyl ether. The pure iridium complex was dried under reduced pressure to give an orange solid (235 mg, 77.3%). Recrystallization from dichloromethane and toluene produced crystals suitable for X-ray crystallography. $^1$H NMR (500 MHz, methylene chloride-d$_2$) δ 8.27 (d, J=4.5 Hz, 1H), 8.10 (t, J=7.5 Hz, 1H), 8.02 (d, J=7.5 Hz, 1H), 7.47 (d, J=5.5 Hz, 1H), 4.89 (s, 2H), 4.51 (s, 2H), 3.66 (d, J=9.1 Hz, 2H), 2.39 (m, 2H), 2.33-2.17 (m, 4H), 1.96 (m, 2H), 1.34 (d, J=13.9 Hz, 18H). $^{13}$C NMR (126 MHz, methylene chloride-d$_2$) δ 169.60 (d, J=20.2 Hz), 149.37, 141.94, 125.25 (d, J=8.8 Hz), 124.74, 90.70, 90.61, 63.70, 37.64 (d, J=20.2 Hz), 34.79 (d, J=25.2 Hz), 33.57, 33.55, 30.27, 30.25, 28.41, 28.40. $^{31}$P NMR (202 MHz, methylene chloride-d$_2$) δ 57.98. $^{19}$F NMR (470 MHz, methylene chloride-d$_2$) 6-78.91. Elemental Analysis (CHNS) Anal. Calcd for C$_{23}$H$_{36}$F$_3$IrNO$_3$PS: C, 40.22; H, 5.28; N, 2.04; S, 4.67. Found: C, 40.54; H, 5.40; N, 2.01; S, 4.63. IR (thin film/cm$^{-1}$) ν 2954, 2889, 2836, 1608, 1475, 1389, 1370, 1319, 1273, 1223, 1148, 1108, 1080, 1031, 1001, 967, 894, 875, 821, 776, 636.

Complex 3b

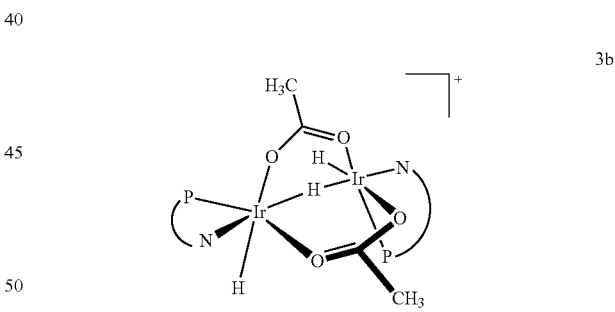

In the drybox under nitrogen, complex 1 (10 mg, 14.9 µmol) was dissolved in 0.6 mL dichloromethane-d$_2$ in a J-Young NMR tube. Dry acetic acid (8.6 µL, 149 µmol) was also added to this solution. The tube was then degassed, put under 1 atm head pressure of H$_2$ gas, and shaken. After ca. 5 minutes, a $^1$H NMR spectrum of the crude reaction mixture was obtained, which confirmed the formation of 2. The solution was then poured into a dry one dram vial. Hexane was carefully layered on top of this DCM solution, and the vial was left in a desiccator for 1 week. A crystal suitable for x-ray diffraction was isolated from the vial. Although the crystal of 3b is stable for days, the pure crystal of 3b re-dissolved in dichloromethane-d$_2$ appears to be in equilibrium with 2 and potentially other form of the iridium complex. $^1$H NMR (600 MHz, methylene chloride-d$_2$):

δ=9.23 (dd, J=5.9, 1.6 Hz, py 2H), 7.93 (tt, J=7.7, 1.4 Hz, py 2H), 7.70 (d, J=7.9 Hz, py 2H), 7.36 (ddd, J=7.4, 5.8, 1.5 Hz, py 2H), 3.58 (dd, J=16.7, 9.6 Hz, methylene 2H), 3.43 (dd, J=16.7, 10.9 Hz, methylene 2H), 2.07 (d, J=1.6 Hz, μ-acetate 6H) 1.25 (d, J=14.0 Hz, tBu 18H), 1.19 (d, J=13.9 Hz, tBu 18H), −26.30 (dd, J=19.0, 3.1 Hz, Ir—H 2H), −28.76 (m, μ-H 1H). $^{13}$C NMR (150 MHz, methylene chloride-$d_2$): δ=184.63 (acetate), 163.84 (py), 149.59 (py), 138.94 (py), 123.42 (py), 123.16 (py), 36.78 (d, J=30.0 Hz, P—C), 36.38 (d, J=27.5 Hz, P—C), 34.88 (d, J=26.9 Hz, P—C), 29.79 (d, J=25.6 Hz, P—C), 28.95 (tBu methyl), 28.69 (tBu methyl), 24.27 (acetate methyl). Other small peaks on the spectrum appeared overtime due to the instability of this compound in solution. $^{31}$P NMR (243 MHz, methylene chloride-$d_2$): δ=44.97. $^{19}$F NMR (564 MHz, methylene chloride-$d_2$): δ=−79.43. IR (thin film/cm$^{-1}$) v 3584, 3441, 2956, 2917, 2238, 2078, 1589, 1479, 1433, 1392, 1371, 1264, 1224, 1158, 1031, 822, 770, 638. MS (MALDI) calc'd for $[C_{30}H_{53}Ir_2N_2O_4P_2]^+$ 951.3 g/mol, found 951.1 g/mol.

Figure 4:
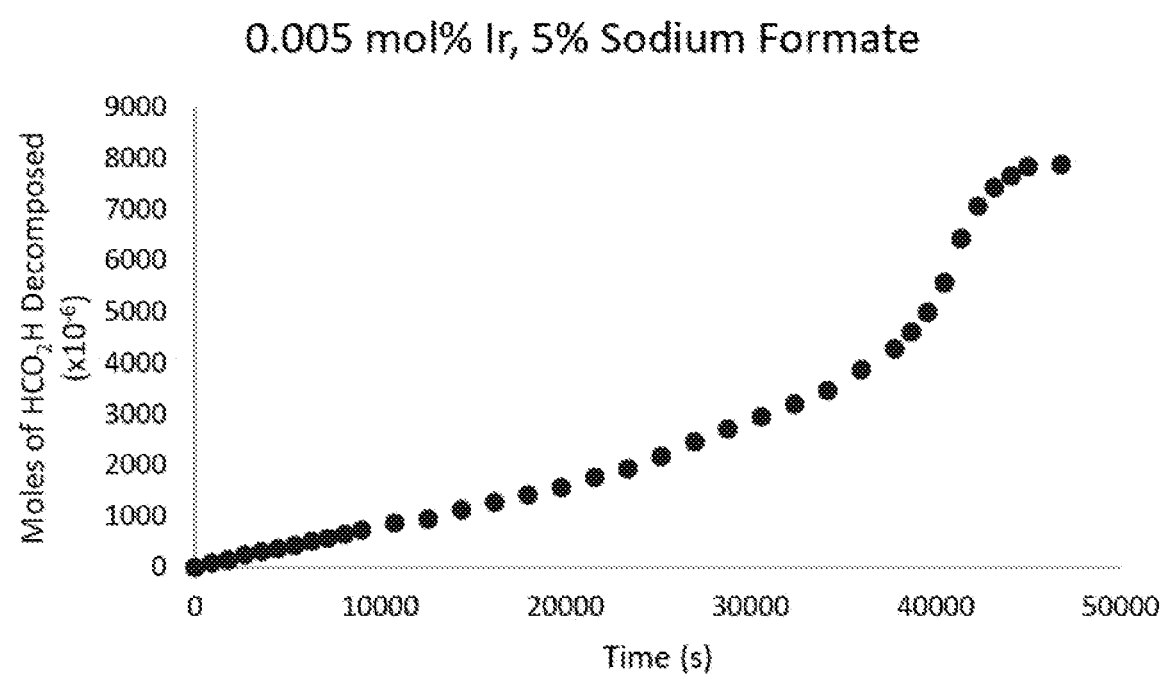
FIG. 4 provides plot of moles of formic acid decomposed versus time at 90° C. with 50 ppm [Ir] and 5 mol % $NaO_2CH$.

The Kinetic Profile for Dehydrogenation of Formic Acid Allows Use of the Method of Initial Rates The dehydrogenation of a formic acid solution which was initially 0.005 mol % (50 ppm) in iridium atoms and 5 mol % in sodium formate was followed (FIG. 4). The volume of gas produced can be recorded and directly converted to the number of moles of formic acid decomposed. One mole of formic acid produces 48.91 L of gas (24.49 L of $H_2$ and 24.42 L of $CO_2$)[2,3]. A plot of moles of formic acid decomposed versus time can then be constructed and the rate of formic acid decomposition at any point over the course of the reaction can be measured. Because the rate is constant at the beginning of the reaction, we can use the method of initial rates to study the reaction order of the three reagents involved in the reaction: the Ir catalyst, the base, and formic acid. We also used the method of initial rates to directly compare the dehydrogenation rates when different bases are utilized, to construct an Eyring plot, to measure kinetic isotope effects, and to determine the effect of water and of different poisons (i.e. mercury and phenanthroline).

Dehydrogenation Rates Using Different Bases

Formic acid stock solutions that were 0.005 mol % (50 ppm) in [Ir atom] and 5 mol % in base were prepared in the drybox by adding measured amounts of the iridium catalyst (1.8 mg, 2.6 μmol) and base (see Table 3 for exact amounts) into a vial. Formic acid (2.0 mL) was then added to dissolve the base and the catalyst. These experiments were aimed to determine the effect of different bases on the rate of dehydrogenation. In addition, these experiments allowed evaluation of the effect on dehydrogenation by the Lewis acids $Li^+$, $Na^+$, $K^+$, and $Ca^{2+}$.

The initial rates of formic acid decomposition (average of two runs) were obtained using Method 2. According to Table 3, base is required for dehydrogenation to occur efficiently. However, the types of bases and Lewis acids do not have an effect on the rate of dehydrogenation. One outlier, the data for calcium carbonate, gives a much lower decomposition rate because copious amounts of calcium formate precipitates.

TABLE 3

Evaluation of the effect of different bases and different Lewis acids on formic acid dehydrogenation.

| Base Used | Added Base (mg) | 1 (ppm) | Base (mol %) | Rate (×10$^{-8}$ mol s$^{-1}$)[a] |
|---|---|---|---|---|
| None | 0 | 50 | 0% | 0.1[b] |
| LiOH[c] | 63 | 50 | 5% | 4.7(1) |
| NaOH[c] | 106 | 50 | 5% | 5.2(1) |
| KOH[c] | 149 | 50 | 5% | 5.4(1) |
| NaO$_2$CH | 180 | 50 | 5% | 6.1(2) |
| KO$_2$CH | 223 | 50 | 5% | 6.4(2) |
| Na$_2$CO$_3$[c] | 140 | 50 | 2.5% | 5.6(3) |
| K$_2$CO$_3$[c] | 183 | 50 | 2.5% | 5.3(5) |
| CaCO$_3$[c,d] | 133 | 50 | 2.5% | 2.5(1) |

[a] Obtained at 86° C.; average of two runs, error is one standard deviation.
[b] Average rate over 5 h; the rate decreases upon further heating.
[c] 2.1 mL of formic acid was added; 0.1 mL reacts with the base.
[d] Copious amounts of precipitates formed.

Effect of Water on the Dehydrogenation Rate

Figure 5:
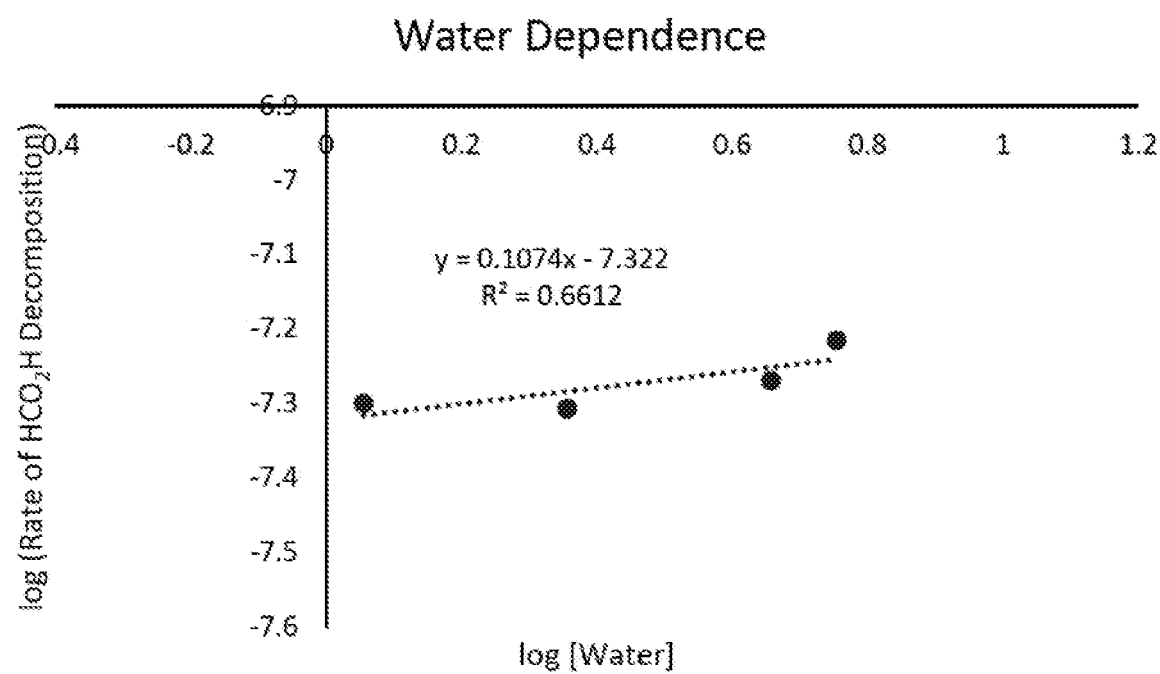
FIG. 5 provides plot of log (rate of formic acid decomposition) versus log [water] in formic acid solvent.

In the drybox, a formic acid stock solution that was 0.005 mol % (50 ppm) in iridium precatalyst 1 and 5 mol % in sodium formate was prepared by dissolving 1.8 mg (2.6 μmol) of 1 and 180 mg (2.64 mmol) of sodium formate in 2.0 mL of formic acid. 0.5 mL of this stock solution was transferred into a 5 mL reaction flask possessing a large bore plug valve and a side arm. Water is added according to the amounts shown in Table 4. Additional formic acid is added accordingly to make a 0.55 mL solution, which was used to measure the rates of formic acid decomposition using Method 2 (see Materials and Methods). A log/log plot of the rate of formic acid decomposition versus the water concentration (FIG. 5) yields a slope of 0.11(5). Thus, water does not inhibit the rate of dehydrogenation.

TABLE 4

Data used to obtain log/log plot for determining reaction order in water (formic acid solvent).

| Water added (μL) | [Water] (M) | [Ir] (mM) | [NaO$_2$CH] (M) | [FA] (M) | Rate (10$^{-8}$ mol s$^{-1}$)[a] |
|---|---|---|---|---|---|
| 10 | 1.14 | 1.14 | 1.14 | 24.96 | 5.0(3) |
| 20 | 2.28 | 1.14 | 1.14 | 24.48 | 4.9(8) |
| 40 | 4.54 | 1.14 | 1.14 | 23.52 | 5.4(6) |
| 50 | 5.68 | 1.14 | 1.14 | 23.04 | 6.1(3) |

[a] Obtained at 86° C.; average of two runs, error is one standard deviation.

Comparison of Dehydrogenation Rates in the Presence and Absence of Air

A formic acid stock solution that is 0.005 mol % in the iridium precatalyst and 5 mol % in sodium was prepared in air by adding 1.8 mg (2.6 μmol) of the iridium precatalyst and 180 mg (2.64 mmol) of sodium formate into a vial. In air, formic acid (2.0 mL) was then added to dissolve the base and the precatalyst. Dehydrogenation rates were obtained 1 day and 2 weeks after preparation of the stock solution using Method 2 (see Materials and Methods). Under otherwise identical conditions, the dehydrogenation of reaction mixtures prepared in air is ca. 3 times slower (Table 5).

TABLE 5

Initial rates of dehydrogenation in the presence and absence of air.

| Experiment | Iridium | NaO$_2$CH | Initial Rate (10$^{-8}$ mol s$^{-1}$) [a] |
|---|---|---|---|
| Air [b] | 0.005% | 5% | 2.1(5) |
| Air [c] | 0.005% | 5% | 1.8(1) |
| No Air [b, d] | 0.005% | 5% | 6.1(2) |

[a] Obtained at 86° C.; average of two runs, error is one standard deviation.
[b] Obtained 1 day after solution preparation.
[c] Obtained 1 day after solution preparation.
[d] Data from Table 4.

Catalyst Reusability in the Presence of Air

A high pressure reaction flask possessing a side arm and a large bore plug valve was charged with the iridium catalyst (6.1 mg, 8.8 µmol) and sodium formate (184.1 mg, 2.7 mmol). In air, formic acid (0.5 mL, 13.2 mmol) was added. The color of the solution slowly changes from orange to pale yellow over the course of 1 hour. The flask was connected to a gas buret and heated to 90° C. Formic acid decomposition was allowed to proceed until mostly solid catalysts remained. The volume of gas produced over time was recorded. The flask was then allowed to cool to room temperature, opened in air, and recharged with 0.5 mL of formic acid. This procedure was repeated dozens of times without significant loss in catalyst activity (Table 6). We measured the initial rates and the maximum turnover frequencies for the 1$^{st}$, 10$^{th}$, 20$^{th}$, 30$^{th}$, 40$^{th}$ and 50$^{th}$ loadings (Table 7). Indeed, the rates and maximum turnover frequencies are comparable and the catalyst activity is still high after the 50$^{th}$ loading. Interestingly, we note that both the initial rates and the maximum turnover frequencies increased over ten cycles before gradually slowing. After 50 loadings, 28.85 L of gas were produced, corresponding to a turnover number of 66,403 and 89% conversion.

TABLE 6

Data showing reusability of the catalyst in air.

| Run | Volume (mL) [a] | Time (min) [b] |
|---|---|---|
| 1 | 417 | 120 |
| 2 | 505 | 90 |
| 3 | 512 | 150 |
| 4 | 513 | 120 |
| 5 | 560 | 120 |
| 6 | 570 | 75 |
| 7 | 541 | 90 |
| 8 | 620 | 90 |
| 9 | 585 | 120 |
| 10 | 619 | 90 |
| 11 | 607 | 80 |
| 12 | 550 | 60 |
| 13 | 605 | 120 |
| 14 | 600 | 90 |
| 15 | 605 | 130 |
| 16 | 585 | 90 |
| 17 | 584 | 90 |
| 18 | 583 | 90 |
| 19 | 580 | 90 |
| 20 | 595 | 80 |
| 21 | 549 | 150 |
| 22 | 540 | 110 |
| 23 | 580 | 90 |
| 24 | 580 | 80 |
| 25 | 530 | 90 |
| 26 | 570 | 90 |
| 27 | 600 | 90 |
| 28 | 610 | 90 |
| 29 | 580 | 75 |
| 30[a] | 565 | 60 |
| 31 | 510 | 120 |
| 32 | 540 | 90 |
| 33 | 620 | 90 |
| 34 | 570 | 120 |
| 35 | 610 | 120 |
| 36 | 600 | 75 |
| 37 | 600 | 75 |
| 38 | 590 | 120 |
| 39 | 565 | 90 |
| 40[a] | 580 | 75 |
| 41 | 600 | 120 |
| 42 | 570 | 120 |
| 43 | 570 | 120 |
| 44 | 560 | 120 |
| 45 | 590 | 120 |
| 46 | 580 | 120 |
| 47 | 640 | 120 |
| 48 | 650 | 120 |
| 49 | 600 | 120 |
| 50[a] | 670 | 120 |

[a] Measured using a 1000 mL gas buret.
[b] Heating was stopped when mostly solid sodium formate and catalyst was present in the reaction flask.

TABLE 7

Catalyst performance over iterative uses.

| Entry | Loading | Initial Rate (µmol s$^{-1}$) [a] | Maximum Turnover Frequency (h$^{-1}$) [b] |
|---|---|---|---|
| 1 | 1$^{st}$ | 0.52 | 1378 |
| 3 | 10$^{th}$ | 2.35 | 3032 |
| 4 | 20$^{th}$ | 2.77 | 2756 |
| 5 | 30$^{th}$ | 2.82 | 2618 |
| 6 | 40$^{th}$ | 2.51 | 2205 |
| 7 | 50$^{th}$ | 1.46 | 1519 |

[a] Obtained from a plot of rate of formic acid decomposition versus time.
[b] Obtained from the highest volume of gas formed over a period of 1 minute.

High Turnover Number and High Turnover Frequency Experiments

High Turnover Number Experiments

In the drybox, a 5 mL high pressure reaction flask with a side arm and a large bore plug valve was charged with sodium formate (0.18 g, 2.64 mmol), which was then dissolved in 0.6 mL of formic acid. A stock solution of the iridium precatalyst (which is actually a stock solution of the iridium dimer catalyst) in formic acid was added (100 µL, 1.26 mM precatalyst stock solution, 0.13 µmol precatalyst).

The reaction flask was taken out of the drybox and connected to a vent line leading to a 1 L gas buret filled with oil. The flask was heated to 90° C. for 24 h. After 24 h, 420 mL of gas was produced. One mole of formic acid decomposes to form 48.91 L of gas (24.49 L of H$_2$ and 24.42 L of CO$_2$). 420 mL of gas produced therefore corresponds to 8.6 mmol of formic acid decomposed and a turnover number of 67,615.

TABLE 8

Data used to obtain maximum turnover number.

| Run | Volume FA Loaded (mL) | Volume of Gas Produced (mL) [a] | Time (h) [b] |
|---|---|---|---|
| 1 | 0.6 | 420 | 24 |
| 2 | 0.6 | 490 | 21 |
| 3 | 0.8 | 560 | 32 |
| 4 | 0.6 | 500 | 26 |
| 5 | 1.0 | 800 | 60 |
| 6 | 0.6 | 420 | 27 |
| 7 | 0.5 | 450 | 27 |
| 8 | 0.5 | 310 | 22 |
| 9 | 0.5 | 410 | 36 |
| 10 | 0.8 | 480 | 60 |
| 11 | 0.3 | 290 | 30 |
| 12 | 0.3 | 290 | 24 |
| 13 | 0.2 | 230 | 16 |
| 14 | 0.2 | 210 | 20 |
| 15 | 0.8 | 460 | 70 |
| 16 | 0.3 | 200 | 24 |
| 17 | 0.3 | 220 | 90 |
| 18 | 0.2 | 160 | 18 |
| 19 | 0.2 | 180 | 20 |
| 20 | 0.6 | 440 | 72 |
| 21 | 0.2 | 160 | 20 |
| 22 | 0.2 | 110 | 16 |
| 23 | 0.2 | 140 | 18 |
| 24 | 0.6 | 360 | 72 |
| 25 | 0.6 | 360 | 72 |
| 26 | 0.6 | 300 | 72 |
| 27 | 0.6 | 310 | 72 |
| 28 | 0.6 | 320 | 72 |
| 29 | 0.6 | 360 | 80 |
| 30 | 0.6 | 290 | 72 |
| 31 | 0.6 | 380 | 80 |
| 32 | 0.6 | 320 | 72 |
| 33 | 0.6 | 400 | 80 |
| 34 | 0.6 | 330 | 72 |
| 35 | 0.6 | 380 | 96 |
| 36 | 0.6 | 300 | 72 |
| 37 | 0.6 | 400 | 120 |
| 38 | 0.6 | 360 | 120 |
| 39 | 0.6 | 310 | 120 |
| 40 | 0.6 | 300 | 120 |

[a] Measured using a 1000 mL gas buret.
[b] Heating was stopped when mostly solid sodium formate and catalyst was present in the reaction flask.

At the end of the reaction, a white solid residue remains at the bottom of the flask. Not all of the formic acid is decomposed because some of the formic acid ends up on the neck and the side arm of the flask and does not mix with the catalyst. Nevertheless, we can recharge the reaction flask with formic acid. To do this, we disconnect the sealed reaction flask from the gas buret, clean the side arm with acetone, and take the flask back into the drybox to be refilled with formic acid. Then we repeat this procedure through 40 cycles. After 40 cycles over a period of 4 months, 13.71 L of gas were produced (Table 8). This corresponds to 0.28 mol of formic acid decomposed and 2.16 M turnovers. The catalyst has slowly lost its catalytic activity. After 4 months, ca. 15% of the initial catalytic activity remains.

High Turnover Frequency Experiment

In the drybox, a 5 mL high pressure reaction flask with a side arm is charged with sodium formate (180 mg, 2.64 mmol) and formic acid (0.3 mL). A stock solution in formic acid of the iridium precatalyst (which is actually a stock solution of the iridium dimer catalyst) was added (100 µL, 1.26 mM precatalyst stock solution, 0.13 µmol precatalyst).

The reaction flask was taken out of the drybox and connected to a 1000 mL gas buret filled with oil. The flask was heated to 90° C. The reaction progress was followed and volume readings were collected towards the end of the reaction, when the rate of formic decomposition was fastest. The fastest rate of gas production recorded was 21 mL over a period of 15 minutes. This corresponds to a maximum turnover frequency of 3.7 $s^{-1}$.

Figure 6A:
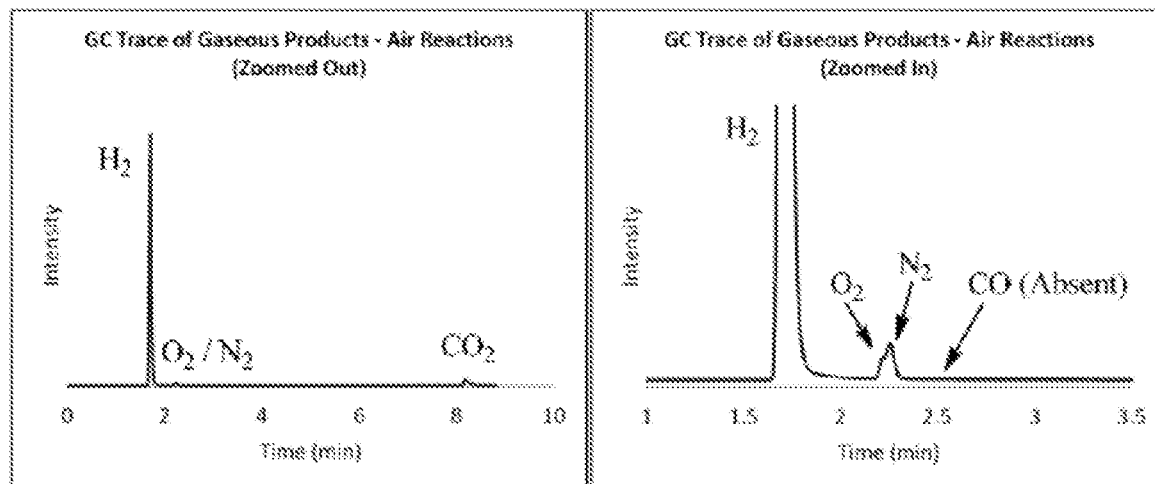
FIG. 6A. GC trace of gaseous products from a dehydrogenation reaction performed in the presence of air.

GC Analysis of the Composition of the Gaseous Products from Formic Acid Dehydrogenation Dehydrogenation in the Presence of Air To a Schlenk test tube containing the iridium precatalyst (5.8 mg, 8.4 µmol) and $NaO_2CH$ (182.6 mg, 2.7 mmol) was added, in air, 0.5 mL of formic acid. The Schlenk test tube was connected to a three-way valve which was connected to a balloon. The reaction flask was heated to 90° C. The gaseous products were collected in the balloon until almost all formic acid was decomposed and their composition analyzed by gas chromatography using a thermal conductivity detector. Three runs were performed. A 1:1 mole ratio of $H_2$ and $CO_2$ was detected along with small amounts of oxygen and nitrogen (FIG. 6A, carbon monoxide was not detected; thus, the carbon monoxide level is <0.099 v/v %).

Dehydrogenation in the Absence of Air

Figure 6B:
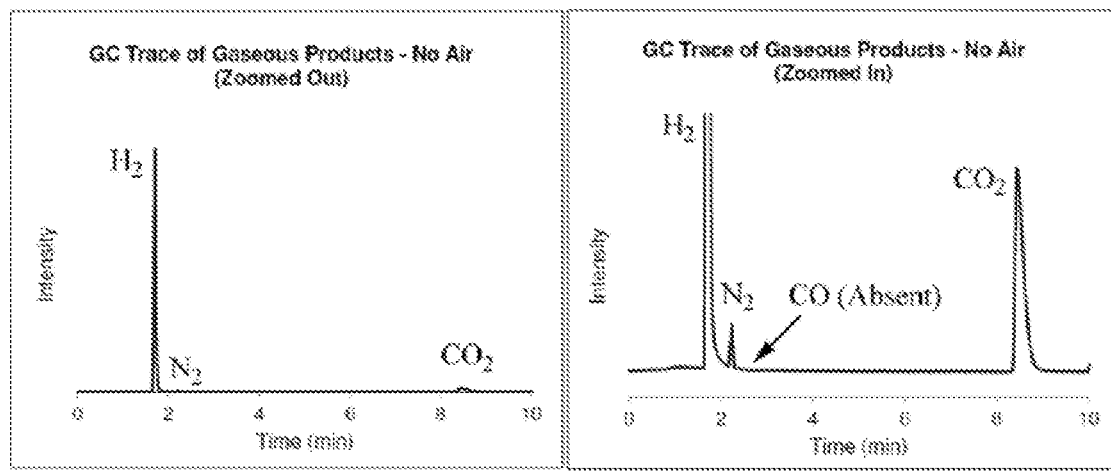
FIG. 6 B. GC trace of gaseous products from a dehydrogenation reaction performed in the absence of air.

In the drybox, a Schlenk test tube containing a solution of the iridium precatalyst (0.7 mg, 1.0 µmol) and $Na_2CO_3$ (85 mg, 0.8 mmol) in 0.35 mL of formic acid was prepared and sealed. The Schlenk test tube was taken out of the drybox and connected to a three-way valve, which was connected to a nitrogen valve and a balloon. The balloon was purged with nitrogen three times. The reaction flask was heated to 110° C. The gaseous products were collected in the balloon, emptying and refilling twice before collecting the sample for analysis in order to remove as much nitrogen gas as possible. The composition of the gaseous products was analyzed by gas chromatography using a thermal conductivity detector. Three runs were performed. A 1:1 mole ratio of $H_2$ and $CO_2$ was detected along with a small amount of residual nitrogen (FIG. 6B, carbon monoxide was not detected; thus, the carbon monoxide level is <0.099 v/v %).

Experiments that Support Homogeneous Catalysis

Visual Appearance

The reaction mixture is a translucent pale yellow solution during catalysis, with no dark precipitates forming. At the end of the reaction, a pale orange solid (the catalysts) remains.

Well Behaved Kinetics

The reaction follows well-behaved saturation catalysis kinetics through its pseudo-zero order region, which persists until solvent level drops appreciably as solvent is consumed (vide infra).

Mercury Drop Test

The mercury drop test was performed by placing 0.5 mL of a formic acid stock solution with 0.01 mol % in iridium precatalyst 1 and 5 mol % sodium formate into a 5 mL reaction flask possessing a large bore plug valve and a side arm. A drop of mercury was then added to this solution. The rate of formic acid decomposition (average of two runs) was then measured to be $1.24 \times 10^{-7}$ mol si at 90° C., which is just slightly slower compared to the measured rate of formic acid decomposition in the absence of mercury ($1.35 \times 10^{-7}$ mol $s^{-1}$).

Quantitative Poisoning

Phenanthroline was utilized as catalytic poison. 1.00 mL (1.26 µmol iridium) of a formic acid solution that is 1.26 mM in iridium atom and 1.26 M in sodium formate was placed in a 2 mL volumetric flask. One-half mole equivalent of the poison relative to the iridium catalyst was added as a stock solution in formic acid (100 µL of 6.3 mM solution, 0.63 µmol). The solution was diluted to 2.00 mL. Using 0.5 mL of this solution, the rate of formic acid decomposition (average of two runs) was then measured to be $1.27 \times 10^{-8}$ mol s$^{-1}$ at 86° C., which is 62% of the formic acid decomposition rate in the absence of phenathroline (which was measured to be $2.04 \times 10^{-8}$ mol s$^{-1}$).

Kinetic Studies on Iridium Dependence in Neat Formic Acid

In the drybox, a formic acid solution that is 5 mol % in sodium formate was prepared by dissolving sodium formate (901 mg, 13.2 mmol) in formic acid (10.0 mL, 265 mmol). To this solution was added the iridium precatalyst (9.1 mg, 13.1 μmol) to make a stock solution that is 0.005 mol % in the precatalyst (1.26 mM, 50 ppm, based on iridium atom).

To set-up solutions for kinetics experiment, in the drybox, 1.0 mL of the catalyst stock solution is transferred via syringe to a 2 mL volumetric flask. A weighed amount of solid catalyst is added (see Table 9 for exact amounts). Formic acid is then added to make 2.00 mL of solution.

Figure 7:
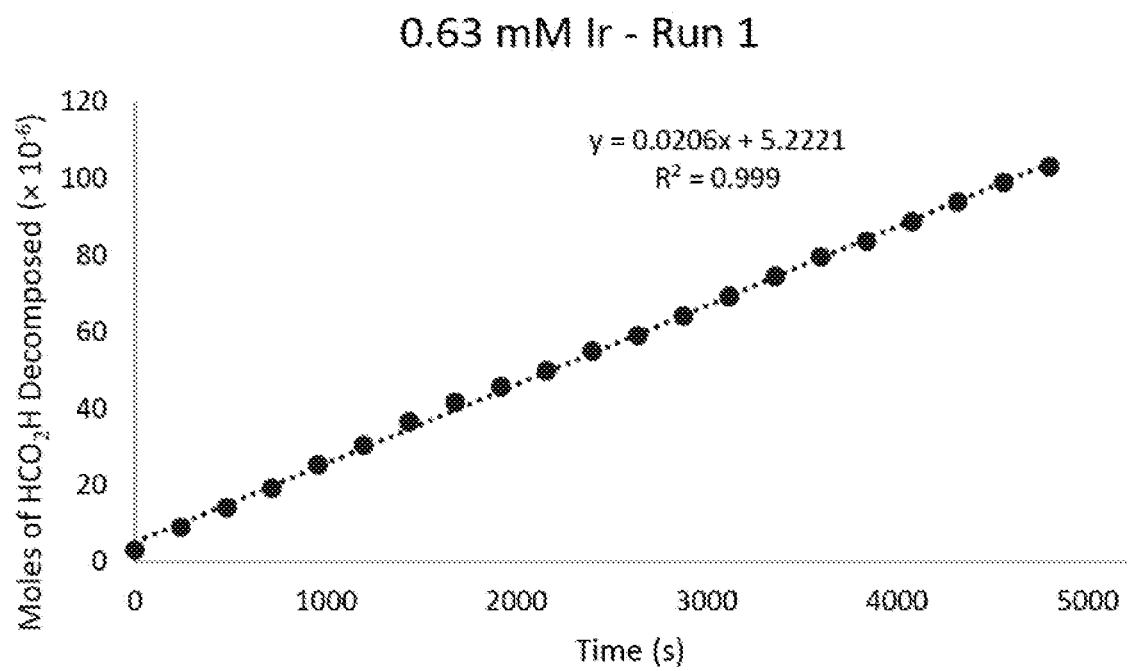
FIG. 7 provides a plot of log (rate of formic acid decomposition) versus log [iridium] in formic acid solvent.

The initial rates of formic acid decomposition were obtained using Method 2 (see Materials and Methods). FIG. 7 is a sample plot showing a constant initial formic acid decomposition rate. Table 9 shows the initial rates at different [Ir]. A plot of log (rate of formic acid decomposition) versus log [Ir] shows that the reaction order is 0.95(3) in iridium catalyst (the error was obtained using Microsoft Excel's LINEST function). Thus, the reaction is first order in iridium.

TABLE 9

Data used to obtain the log/log plot for determining reaction order in iridium (formic acid solvent).

| Additional mass of Ir added (mg) | [Ir] in reaction mixture (mM) | [NaO$_2$CH] in reaction mixture (M) | [FA] in reaction mixture (M) | Rate of HCO$_2$H Decomposition ($10^{-8}$ mol s$^{-1}$) [a] |
|---|---|---|---|---|
| 0 | 0.63 | 0.63 | 25.9 | 2.0(1) |
| 1.7 | 1.86 | 0.63 | 25.9 | 6.0(6) |
| 2.7 | 2.59 | 0.63 | 25.9 | 8.0(2) |
| 3.6 | 3.25 | 0.63 | 25.9 | 9.3(5) |
| 5.2 | 4.41 | 0.63 | 25.9 | 13(1) |

[a] Obtained at 86° C.; average of two runs, error is one standard deviation.

Kinetic Studies on Sodium Formate Dependence in Neat Formic Acid

In the drybox, a formic acid stock solution that is 0.53 mM in sodium formate was prepared by dissolving sodium formate (360 mg, 5.3 mmol) in formic acid (10.0 mL, 265 mmol). To this solution was added iridium complex 1 (9.1 mg, 13.1 μmol).

To set up solutions for kinetics experiments, 1.0 mL of the catalyst stock solution is transferred via syringe to a 2 mL volumetric flask in the drybox. A portion of sodium formate is added (see Table 10). Formic acid is then added to make 2.00 mL of solution.

Figure 8:
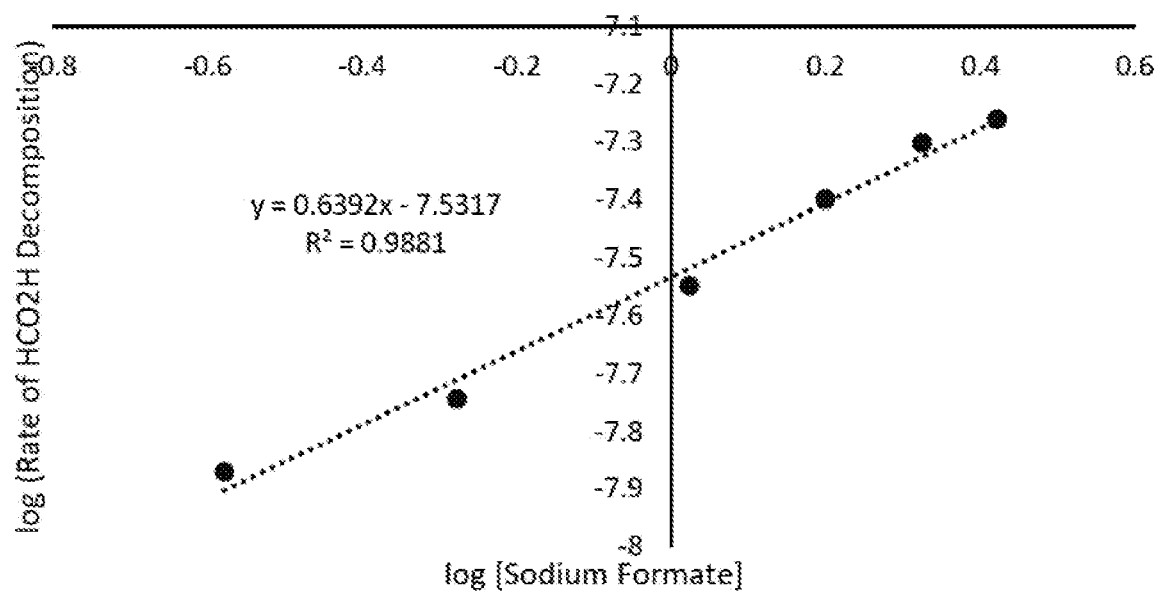
FIG. 8 provides a plot of log (rate of formic acid decomposition) versus log [sodium formate] in formic acid solvent.

The initial rates of formic acid decomposition were obtained using Method 2 (see Materials and Methods). Table 10 shows the initial rates at different [NaO$_2$CH]. A plot of log (rate of formic acid decomposition) versus log [NaO$_2$CH] shows that the reaction order is 0.64(5) in sodium formate (FIG. 8). Thus, the reaction is half-order in NaO$_2$CH.

TABLE 10

Data used to obtain the log/log plot for determining reaction order in sodium formate (formic acid solvent).

| Added NaO$_2$CH (mg) | [Ir] (mM) | [NaO$_2$CH] (M) | [FA] (M) | Rate ($10^{-8}$ mol s$^{-1}$) [a] |
|---|---|---|---|---|
| 0 | 0.66 | 0.26 | 26.26 | 1.4(3) |
| 72 | 0.66 | 0.53 | 26.01 | 1.8(1) |
| 144 | 0.66 | 1.06 | 25.51 | 2.8(1) |
| 216 | 0.66 | 1.59 | 25.01 | 3.6(2) |
| 288 | 0.66 | 2.11 | 24.51 | 5.3(1) |
| 360 | 0.66 | 2.65 | 24.01 | 6.0(4) |

[a] Obtained at 86° C.; average of two runs, error is one standard deviation.

Kinetic Studies on Iridium Dependence in Tetraglyme Solvent

In the drybox, a stock solution of iridium in tetraglyme (2.64 mM) was prepared by dissolving the iridium precatalyst 1 (18.2 mg, 26.46 mmol) in a volumetric flask to make 10.00 mL of stock solution in tetraglyme.

Because sodium formate is insoluble in tetraglyme, we generated soluble (n-Bu)$_4$N(HCO$_2$) by deprotonating formic acid with 1.20 M (n-Bu)$_4$N(OH) in methanol. (n-Bu)$_4$N(OH) was titrated using benzoic acid and bromothymol blue as indicator.

To set-up solutions for kinetics experiments, a 2 mL volumetric flask is filled with ca. 1 mL of tetraglyme in the drybox. Then 22 μL of 1.21 M (n-Bu)$_4$N(OH) in methanol and 21 μL of formic acid are added and the solution thoroughly mixed. A measured amount of the iridium catalyst stock solution (see Table 11) is added and the solution thoroughly mixed. The color of the solution changes immediately from orange to very pale yellow. Tetraglyme is then added to make 2.00 mL of solution.

Figure 9:
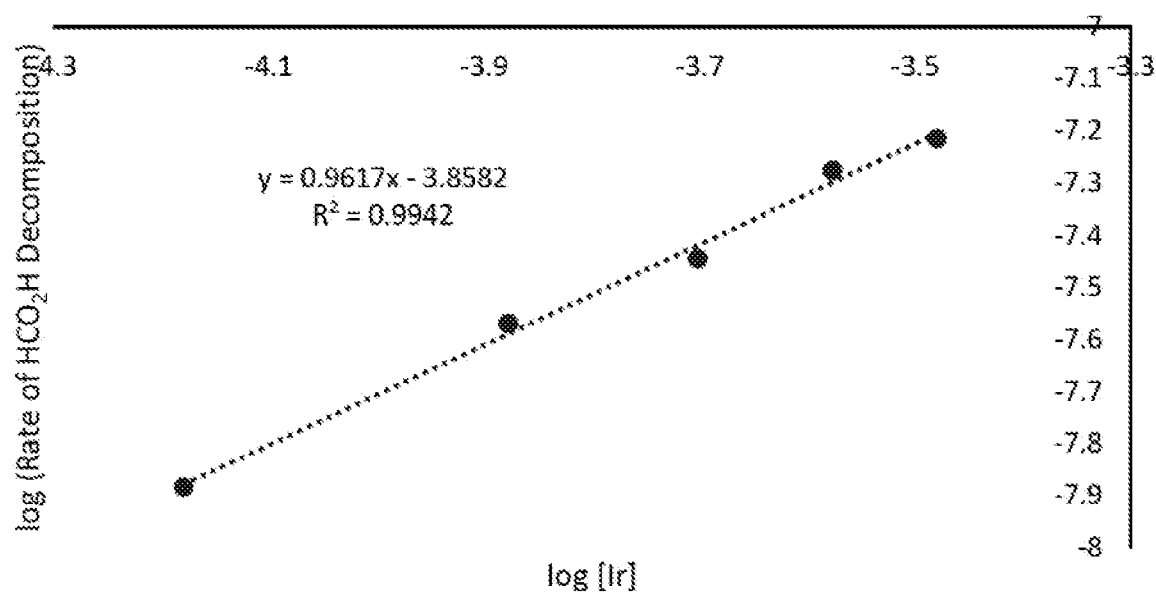
FIG. 9 provides a plot of log (rate of formic acid decomposition) versus log [iridium] in tetraglyme solvent.

Using this freshly prepared solution, the initial rates of formic acid decomposition were obtained using Method 2 (see Materials and Methods), except that a Schlenk test tube with a side-arm is utilized instead of a 5 mL high pressure reaction vessel. Table 11 shows the initial rates at different [Ir]. A plot of log (rate of formic acid decomposition) versus log [Ir] shows that the reaction order is 0.96(4) in iridium catalyst (FIG. 9). Thus, the reaction is first order in iridium.

TABLE 11

Data used to obtain log/log plot for determining reaction order in iridium (tetraglyme solvent).

| FA added | (nBu)$_4$N(OH) solution | Ir solution | [Ir] (μM) | [(nBu)$_4$N(O$_2$CH)] (mM) | [FA] (mM) | Rate ($10^{-8}$ mol s$^{-1}$) [a] |
|---|---|---|---|---|---|---|
| 21 μL, 0.53 mmol | 22 μL, 26.4 μmol | 50 μL, 0.13 μmol | 66 | 13.2 | 265 | 1.3(1) |
| 21 μL, 0.53 mmol | 22 μL, 26.4 μmol | 100 μL 0.26 μmol | 130 | 13.2 | 265 | 2.7(2) |
| 21 μL, 0.53 mmol | 22 μL, 26.4 μmol | 150 μL 0.39 μmol | 200 | 13.2 | 265 | 3.6(2) |
| 21 μL, 0.53 mmol | 22 μL, 26.4 μmol | 200 μL 0.52 μmol | 260 | 13.2 | 265 | 5.3(1) |

TABLE 11-continued

Data used to obtain log/log plot for determining reaction order in iridium (tetraglyme solvent).

| FA added | (nBu)$_4$N(OH) solution | Ir solution | [Ir] (μM) | [(nBu)$_4$N(O$_2$CH)] (mM) | [FA] (mM) | Rate (10$^{-8}$ mol s$^{-1}$)[a] |
|---|---|---|---|---|---|---|
| 21 μL, 0.53 mmol | 22 μL, 26.4 μmol | 250 μL 0.65 μmol | 330 | 13.2 | 265 | 6.1(1) |

[a] Obtained at 86° C.; average of two runs, error is one standard deviation.

Kinetic Studies on Tetra-n-Butylammonium Formate Dependence in Tetraglyme

In the drybox, a stock solution of the iridium precatalyst in tetraglyme (1.32 mM) was prepared by dissolving the iridium precatalyst (9.1 mg, 13.23 mmol) in a volumetric flask to make 10.00 mL of solution.

Figure 10:
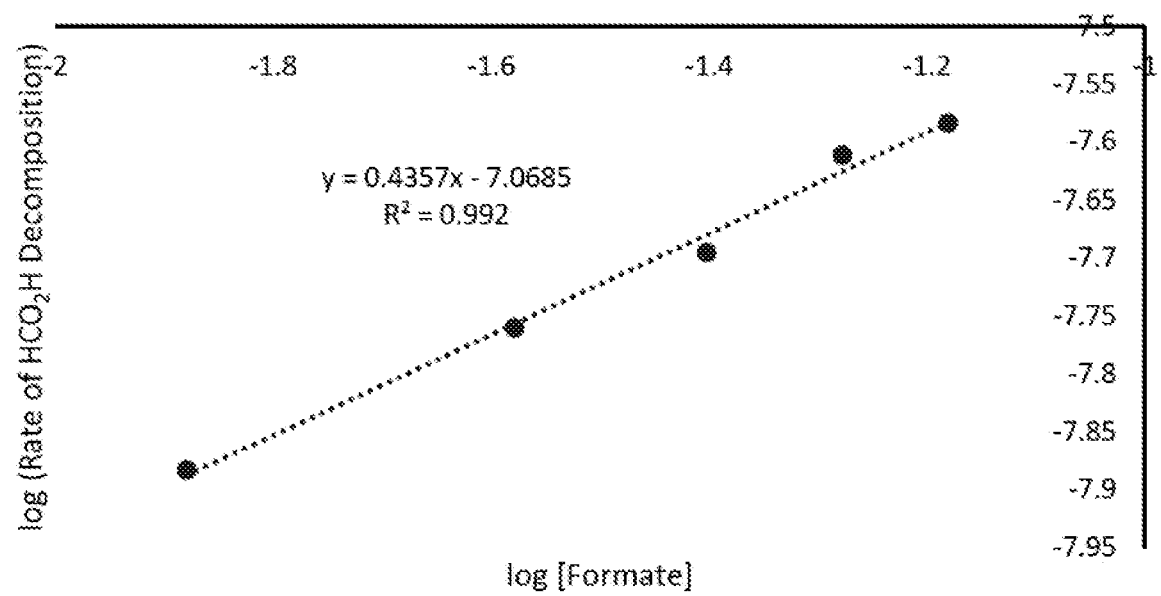
FIG. 10 provides a plot of log (rate of formic acid decomposition) versus log [formate] in tetraglyme solvent.

Using this stock solution, kinetics data were obtained according to the procedure described in Section S13 except that (n-Bu)$_4$N(O$_2$CH) concentration was varied instead of iridium concentration. Also, methanol was added so that each solution had the same amount of methanol. The concentrations of (n-Bu)$_4$N(O$_2$CH) used are shown in Table 12. A log/log plot of rate of formic acid decomposition versus (n-Bu)$_4$N(O$_2$CH) concentration shows a reaction order of 0.44(2) (FIG. 10). This indicates a reaction order of 0.5 with respect to (n-Bu)$_4$N(O$_2$CH).

TABLE 12

Data used to obtain log/log plot for determining reaction order in formate (tetraglyme solvent).

| FA added | (nBu)$_4$N(OH) solution | Ir solution | [Ir] (μM) | [(nBu)$_4$N(O$_2$CH)] (mM) | [FA] (mM) | Rate (10$^{-8}$ mol s$^{-1}$)[a] |
|---|---|---|---|---|---|---|
| 21 μL, 0.53 mmol | 22 μL, 26.4 μmol | 100 μL 0.13 μmol | 66 | 13.2 | 265 | 1.3(1)[b] |
| 22 μL, 0.53 mmol | 44 μL, 52.8 μmol | 100 μL 0.13 μmol | 66 | 26.4 | 265 | 1.7(1) |
| 23 μL, 0.53 mmol | 66 μL, 79.2 μmol | 100 μL 0.13 μmol | 66 | 39.6 | 265 | 2.0(1) |
| 24 μL, 0.53 mmol | 88 μL, 105.6 μmol | 100 μL 0.13 μmol | 66 | 52.8 | 265 | 2.4(1) |
| 25 μL, 0.53 mmol | 110 μL, 132 μmol | 100 μL 0.13 μmol | 66 | 66.0 | 265 | 2.6(1) |

[a] Obtained at 86° C.; average of two runs, error is one standard deviation.

Kinetic Studies on Formic Acid Dependence in Tetraglyme Solvent

In the drybox, a stock solution of the iridium precatalyst in tetraglyme (2.64 mM) was prepared by dissolving the iridium precatalyst (18.2 mg, 26.46 mmol) in a volumetric flask to make 10.00 mL of solution.

Figure 11:
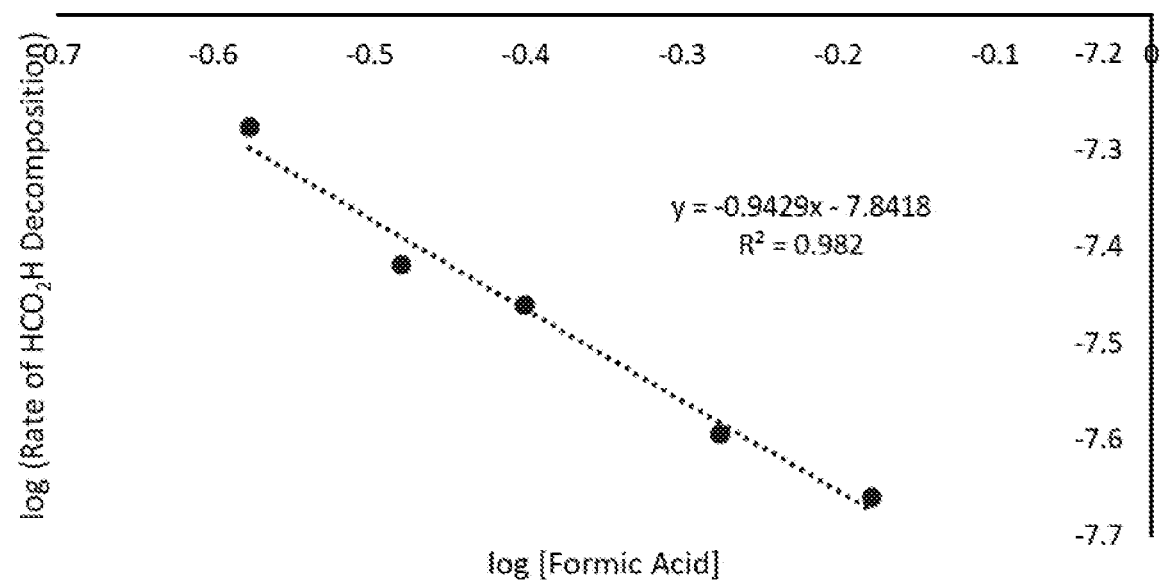
FIG. 11 provides a plot of log (rate of formic acid decomposition) versus log [formic acid] in tetraglyme solvent.

Using this stock solution, kinetics data were obtained according to the procedure described in above except that formic acid concentration was varied instead of iridium concentration. The concentrations of formic acid used are shown in Table 13. A log/log plot of rate of formic acid decomposition versus formic acid concentration shows a reaction order of −0.94(9) (FIG. 11). This indicates a reaction order of −1.0 with respect to formic acid.

TABLE 13

Data used to obtain log/log plot for determining reaction order in formic acid (tetraglyme solvent).

| FA added | (nBu)$_4$N(OH) solution | Ir solution | [Ir] (μM) | [(nBu)$_4$N(O$_2$CH)] (mM) | [FA] (mM) | Rate (10$^{-8}$ mol s$^{-1}$)[a] |
|---|---|---|---|---|---|---|
| 21 μL, 0.53 mmol | 22 μL, 26.4 μmol | 200 μL 0.52 μmol | 260 | 13.2 | 265 | 5.3(1)[b] |
| 26 μL, 0.66 mmol | 22 μL, 26.4 μmol | 200 μL 0.52 μmol | 260 | 13.2 | 331 | 3.8(2) |
| 31 μL, 0.80 mmol | 22 μL, 26.4 μmol | 200 μL 0.52 μmol | 260 | 13.2 | 398 | 3.5(1) |
| 41 μL, 1.06 mmol | 22 μL, 26.4 μmol | 200 μL 0.52 μmol | 260 | 13.2 | 530 | 2.6(1) |

TABLE 13-continued

Data used to obtain log/log plot for determining reaction order in formic acid (tetraglyme solvent).

| FA added | (nBu)$_4$N(OH) solution | Ir solution | [Ir] (μM) | [(nBu)$_4$N(O$_2$CH)] (mM) | [FA] (mM) | Rate (10$^{-8}$ mol s$^{-1}$)$^a$ |
|---|---|---|---|---|---|---|
| 51 μL, 1.32 mmol | 22 μL, 26.4 μmol | 200 μL 0.52 μmol | 260 | 13.2 | 662 | 2.2(1) |

$^a$Obtained at 86° C.; average of two runs, error is one standard deviation.

Eyring Plot

In the drybox, a formic acid solution that is 5 mol % in sodium formate was prepared by dissolving sodium formate (901 mg, 13.2 mmol) in formic acid (10.0 mL, 265 mmol). To this solution was added the iridium precatalyst (18.2 mg, 26.2 μmol) to make a stock solution of the catalyst (2.52 mM based on monoiridium). The solution is allowed to sit overnight before use.

Figure 12:
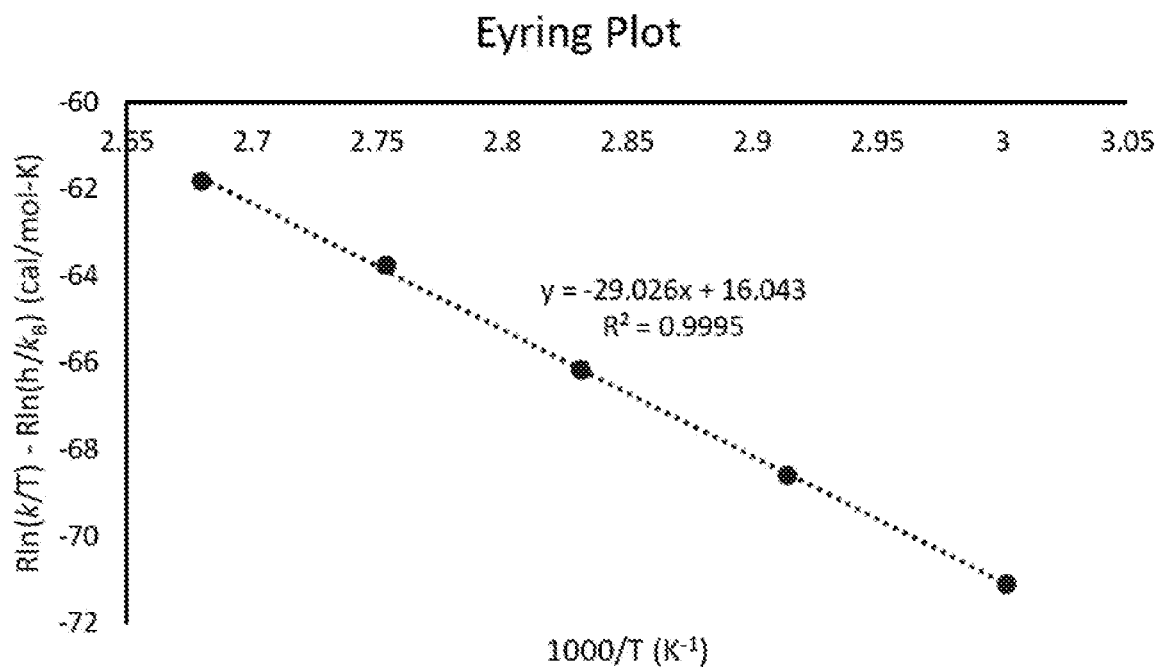
FIG. 12 provides an Eyring plot for dehydrogenation.

The initial rates of formic acid decomposition were obtained using Method 2 (see Materials and Methods). Table 14 shows the initial rates and turnover frequencies at 60, 70, 80, 90, and 100° C. An Eyring plot was constructed utilizing the measured turnover frequencies (FIG. 12). From the Eyring plot, $\Delta H^\ddagger=+29.0(4)$ kcal mol$^{-1}$ and $\Delta S^\ddagger=+16.0(10)$ eu.

TABLE 14

Data used for the Eyring plot.

| Temperature (° C.) | Rate (10$^{-9}$ mol s$^{-1}$)$^a$ | Turnover Frequency (10$^{-3}$ s$^{-1}$)$^b$ |
|---|---|---|
| 60 | 2.5(2) | 2.0 |
| 70 | 9(1) | 7.2 |
| 80 | 32(2) | 24.9 |
| 90 | 109(3) | 86.1 |
| 100 | 296(5) | 233.8 |

$^a$ Obtained at 86° C.; average of two runs, error is one standard deviation.
$^b$ Obtained by dividing the rate of formic acid decomposition with the moles of iridium precatalyst in a 0.5 mL aliquot of the stock solution (2.52 mM in iridium).

Kinetic Isotope Effect Studies

To obtain values for $k_H/k_D$, the initial rates of dehydrogenation using formic acid, formic acid-d$_2$, formic acid-d$_1$ (O-D), and formic acid-d$_1$ (C-D) were obtained.

Stock solutions of formic acid, formic acid-d$_2$, formic acid-d$_1$ (C-D), and formic acid-d$_1$ (O-D) that were 0.005 mol % (50 ppm) in iridium precatalyst 1 and 5 mol % in formate were prepared. In the drybox, a vial was charged with 1.8 mg (2.6 μmol) of the iridium precatalyst and 180 mg of either sodium formate (for the FA and FA-d$_1$ (O-D) solutions) or sodium formate-d$_1$ (for the FA-d$_2$ and FA-d$_1$ (C-D) solutions). The appropriate proteo/deutero formic acid (2.0 mL) was then added to dissolve the base and the precatalyst. The solution was allowed to sit overnight before use. The initial rates of formic acid decomposition were obtained using Method 2 (see Materials and Methods). Table 15 shows the initial rates of dehydrogenation using different isotopologues of formic acid. See main text for the obtained kinetic isotope effects.

TABLE 15

Data for kinetic isotope effect studies.

| Compound | Rate (10$^{-8}$ mol s$^{-1}$)$^a$ |
|---|---|
| HCO$_2$H | 6.1(2) |
| HCO$_2$D | 1.55(14) |
| DCO$_2$H | 3.4(2) |
| DCO$_2$D | 0.94(2) |

$^a$ Obtained at 86° C.; average of two runs, error is one standard deviation.

Proton-Hydride Fidelity Experiment

Figure 13A:
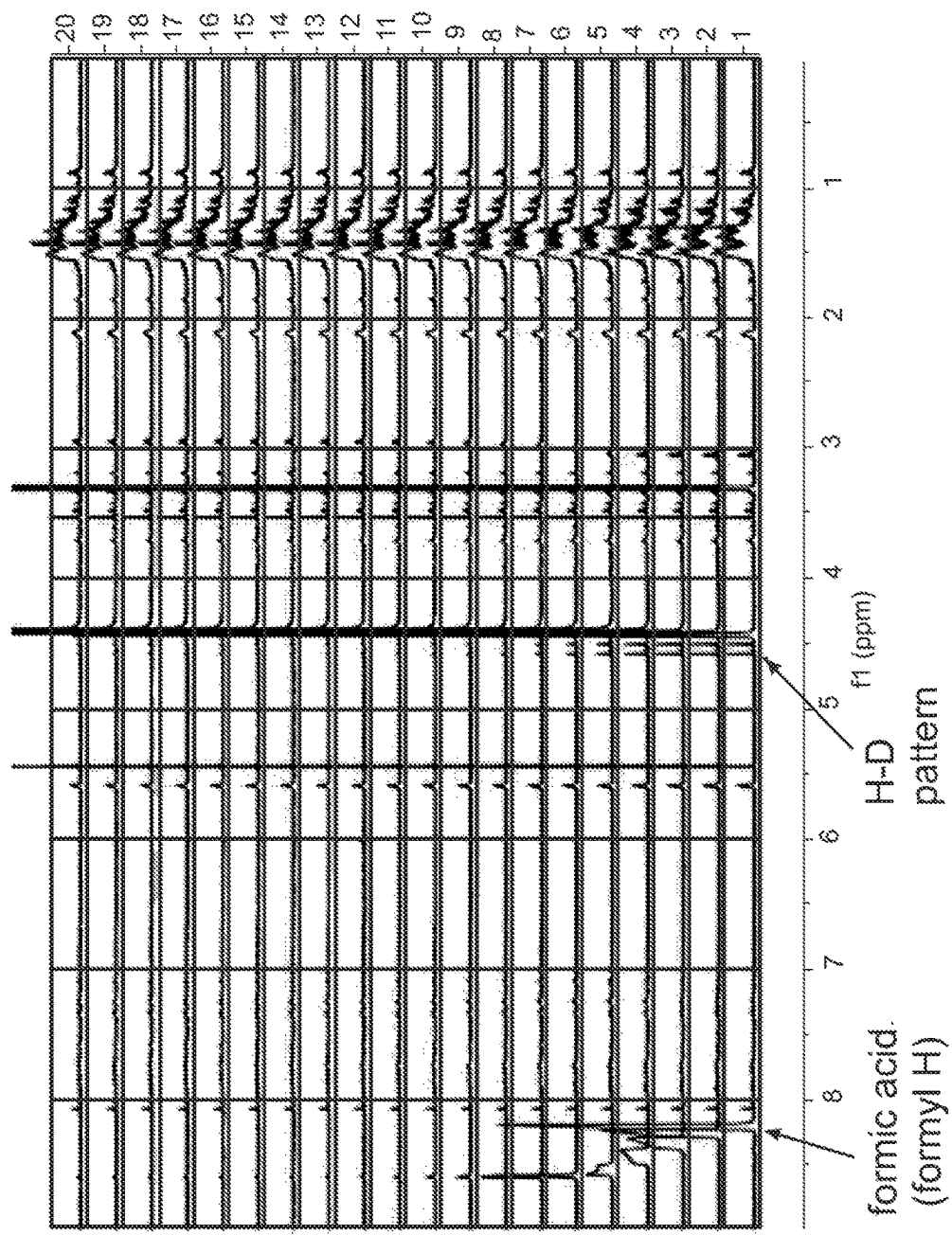
FIG. 13A provides a time course $^1H$ NMR experiment showing H-D formation.
Figure 13B:
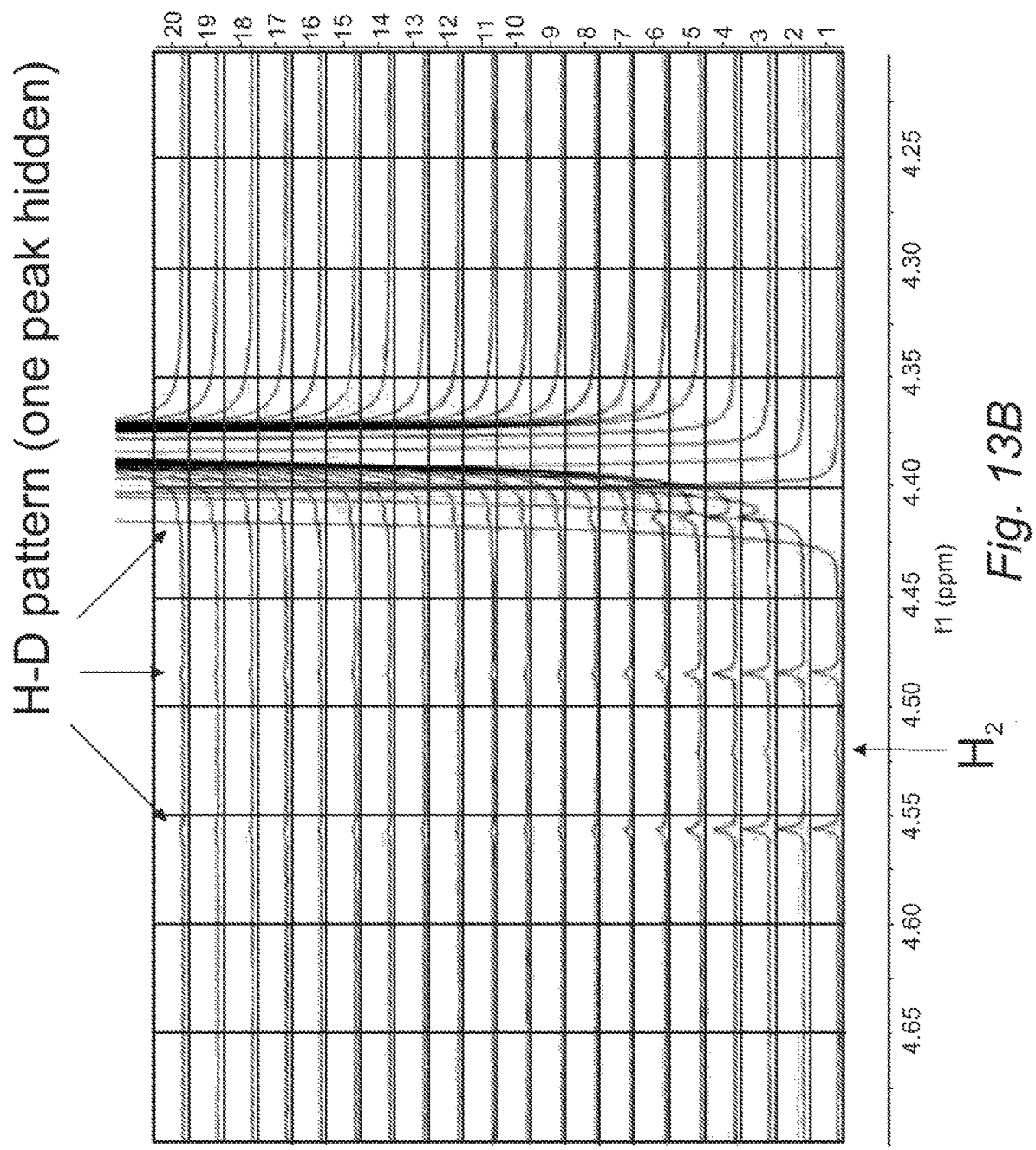
FIG. 13B provides a zoomed in region of a time course $^1H$ NMR experiment showing H-D formation more clearly showing H-D formation.

In the drybox, a J-Young tube was charged with the iridium precatalyst (1.8 mg, 2.64 mol), sodium formate (1.7 mg, 25.0 μmol), formic acid-d$_1$ (O-D; 5 μL, 0.13 mmol), and 0.6 mL of methanol-d$_4$. A $^1$H NMR time course experiment spanning over 72 minutes was performed at 70° C. Before the time course experiment was initiated, the NMR tube had been heated ca. 10 minutes at 70° C. and much H-D had formed (FIG. 13). Nevertheless, formation of predominantly H-D with a small amount of H$_2$ is observed. This observation is consistent with a formic acid dehydrogenation mechanism that proceeds through formation of an iridium monohydride where the hydride comes from the formyl C—H bond of formic acid. This iridium monohydride is then protonated (or, technically, deuterated) by the formic acid O-D. We expect that an iridium dihydride that undergoes reductive elimination to yield H$_2$ should enable scrambling of proton and hydride, thus we disfavor this possibility. The small amount of H$_2$ that forms can be rationalized by the presence of small amounts of formic acid O—H bonds which protonates the iridium monohydride. Interestingly, the HD signal disappears after extended heating, which is consistent with a slow reverse reaction when the reaction is run in a sealed vessel. Such back reaction is impossible under our kinetics acquisition conditions because the H$_2$ product is sequestered and quantified in an eudiometer.

Observation of Catalyst Intermediates by NMR

Data regarding the elementary steps of the conversion of the precatalyst to the active dimer catalyst were obtained using NMR. We can observe the formation of a dimer (2) from precatalyst 1 in two different ways: 1) reaction of 1 with formic acid in a coordinating solvent such as acetonitrile or 2) reaction of 1 with H$_2$ in various solvents. In formic acid solvent, iridium dimer 2 is converted further into the (di-μ-formate)iridium dimer 3a.

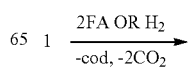

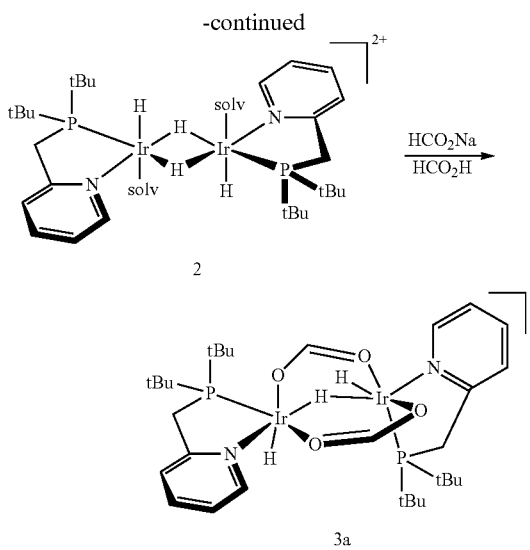

2

3a

Observation of Intermediate 2 in CD₃CN

Figure 14:
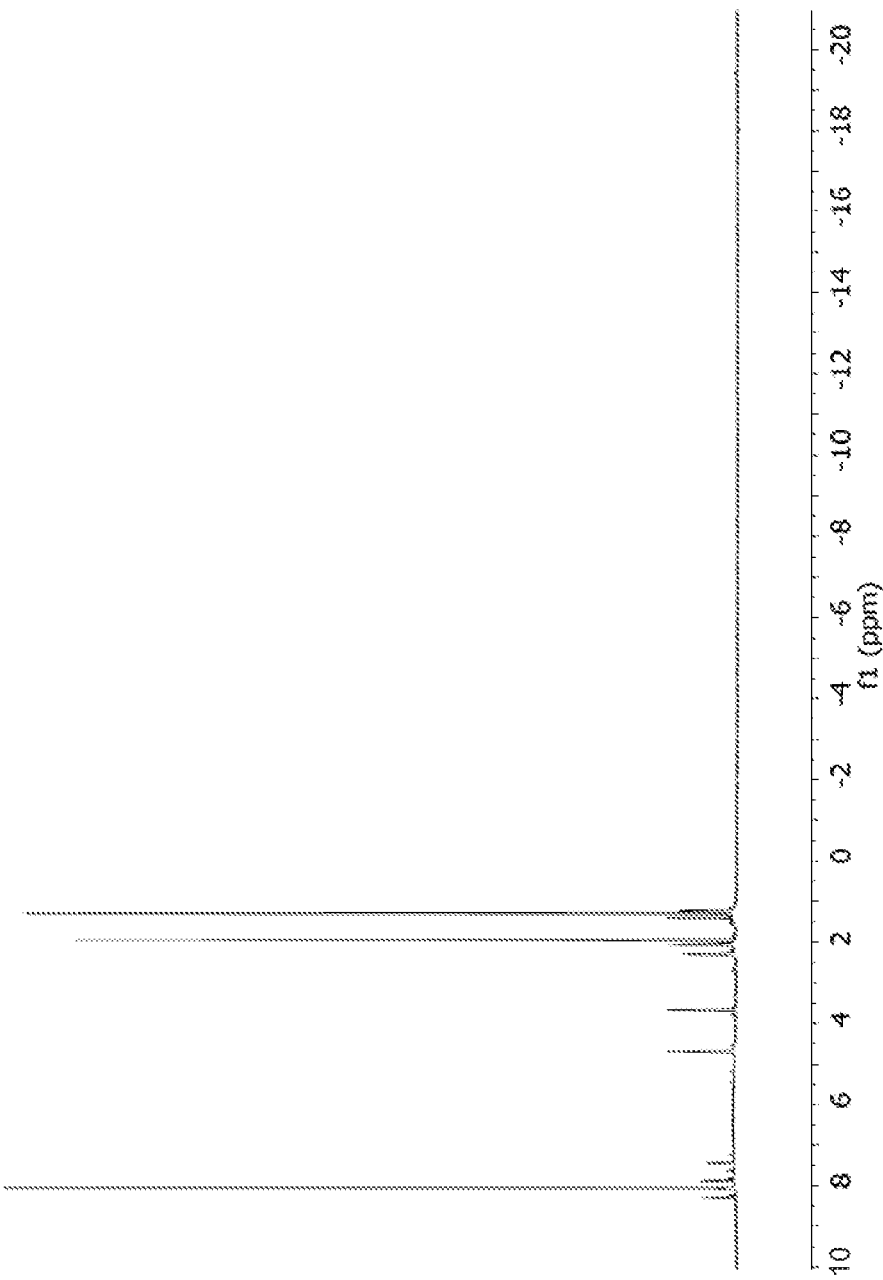
FIG. 14 provides $^1H$ NMR spectrum of precatalyst 1 ca. 15 min after addition of 1 equiv. of sodium formate and 10 equiv formic acid ($CD_3CN$ solvent)
Figure 15:
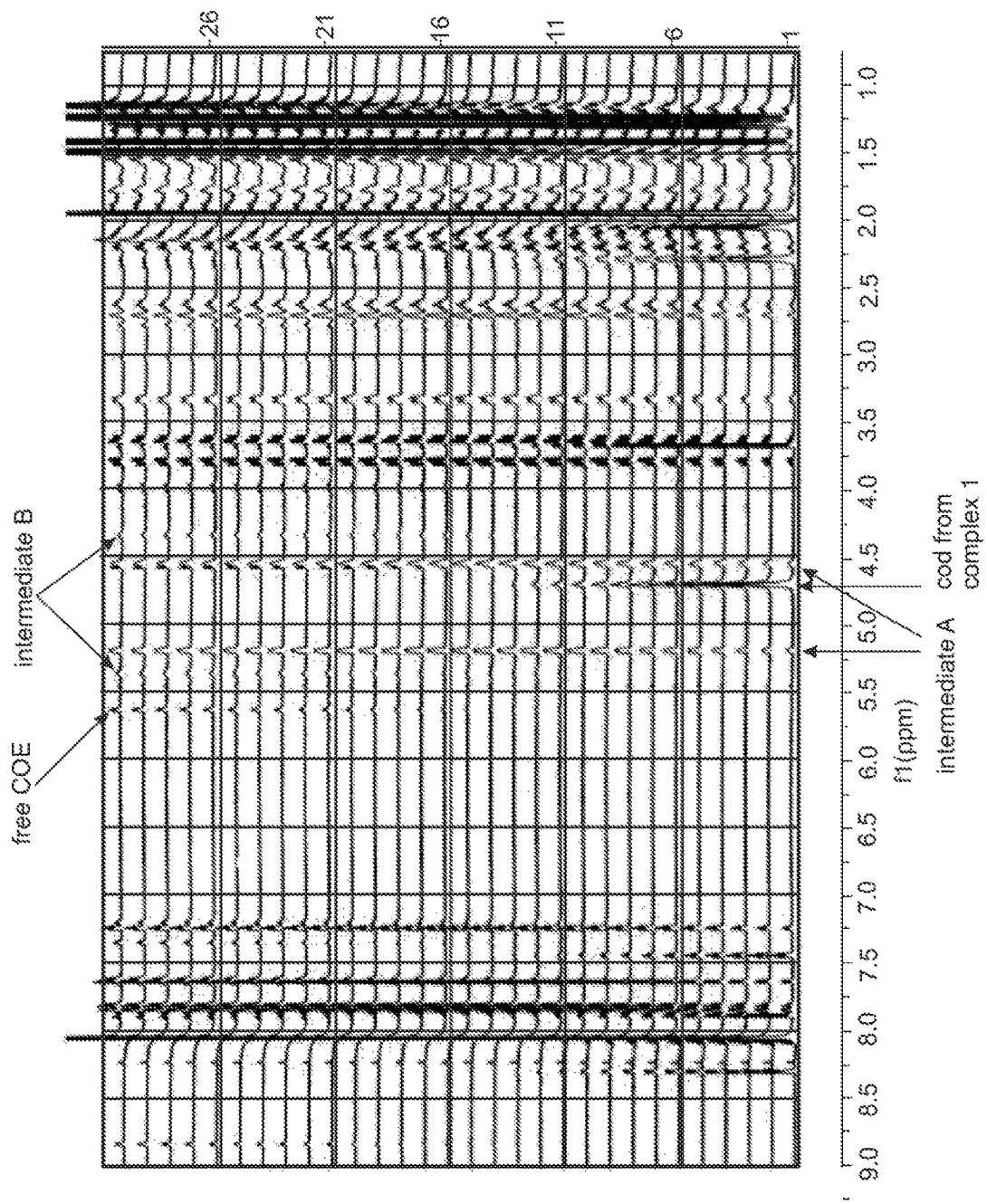
FIG. 15 provides an $^1H$ NMR time course experiment began ca. 20 min after addition of 1 equiv of sodium formate and 10 equiv formic acid ($CD_3CN$ solvent)
Figure 16:
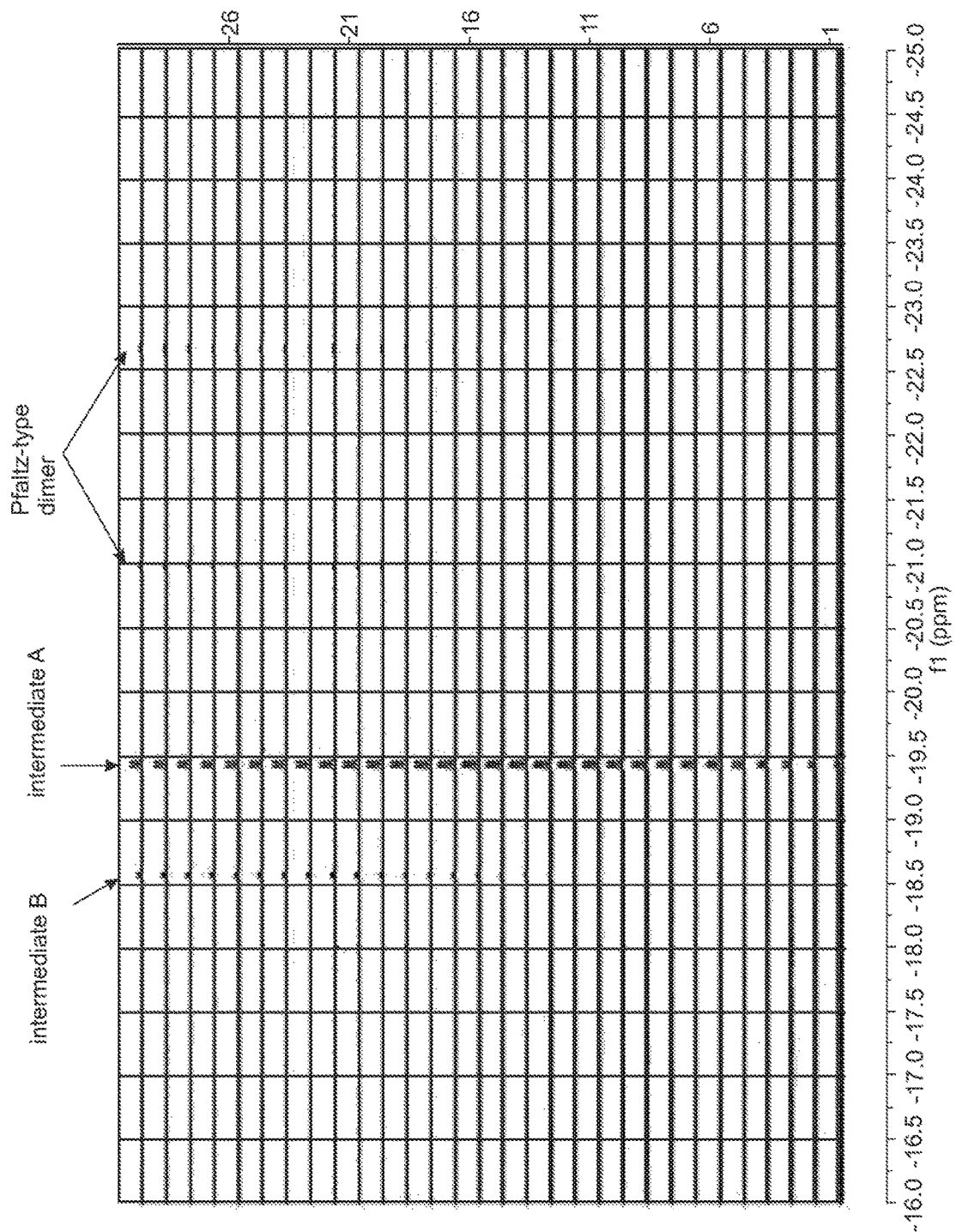
FIG. 16 provides a $^1H$ NMR time course experiment (hydride region) began ca. 20 min after addition of 1 equiv of sodium formate and 10 equiv formic acid ($CD_3CN$ solvent)
Figure 17:
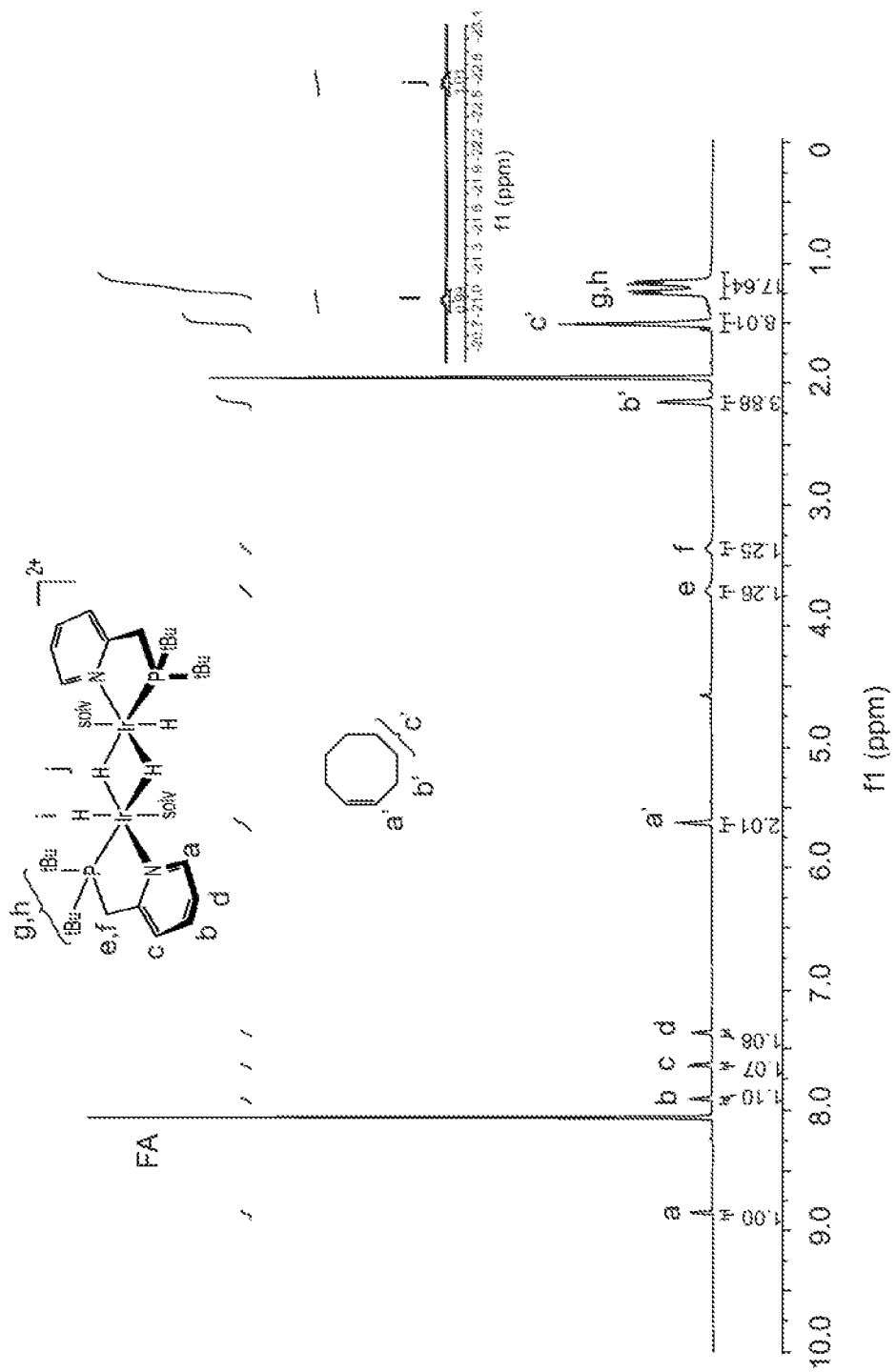
FIG. 17 provides a $^1H$ NMR spectrum of the products in the reaction of precatalyst 1 with FA in $CD_3CN$: A Pfaltz-type dimer and cyclooctene.

Room temperature ¹H NMR studies in CD₃CN show that addition of 1 equivalent of sodium formate and 10 equivalents of formic acid to a solution of iridium precatalyst 1 leads to formation of a new species (intermediate A) with a hydride signal at −19.43 ppm (FIG. 14-FIG. 16). Data for this species is consistent with oxidative addition of formic acid to the iridium precatalyst. 20 minutes after addition of sodium formate and formic acid, a time course experiment was collected over a period of 66 min (FIG. 15 and FIG. 16). The resulting stacked ¹H NMR spectra shows that intermediate A grows then intermediate B appears ca. 30 min after addition of sodium formate and formic acid. Intermediate B is consistent with a species where one of the cyclooctadiene double bonds is bound to iridium and the other is free. Then the product appears ca. 1 hour after addition. The ¹H NMR spectrum of the final product is consistent with dimer 2 (FIG. 17; S=CD₃CN). The cyclooctadiene in the iridium precatalyst is reduced to cyclooctene and free cyclooctene is seen in the ¹H NMR spectrum of the products. Although 3 does not form in CD₃CN, it is reasonable to conclude that formation of the catalyst resting state (diformate 3a) proceeds in a similar fashion through the intermediacy of 2 when formic acid or tetraglyme is used as solvent. It is worth noting that, in CD₃CN, iridium 1 reacts in the absence of base with formic acid to form 2, but in a much slower rate.

Figure 18:
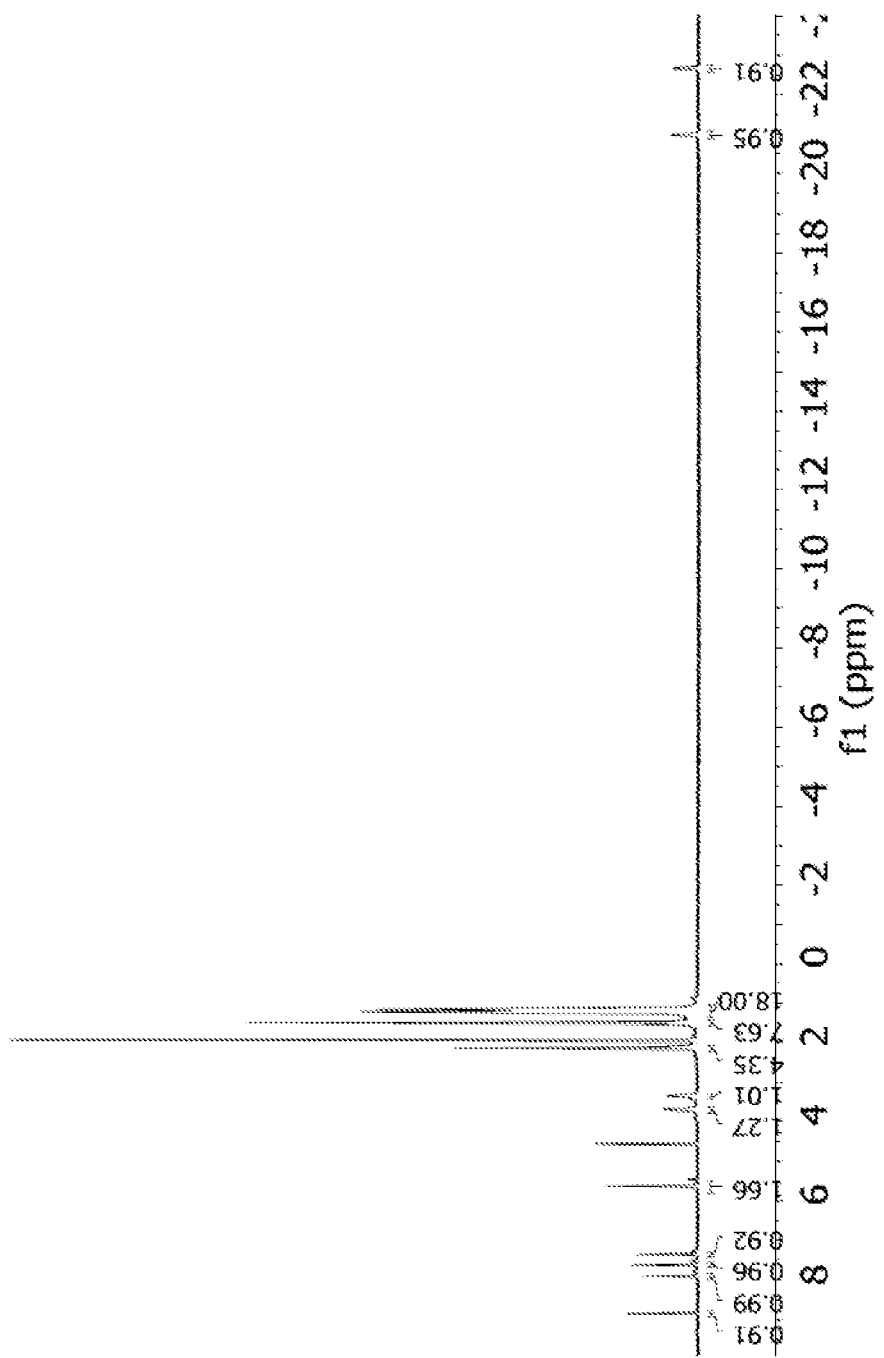
FIG. 18 provides a $^1H$ NMR spectrum of the products in the reaction of precatalyst 1 with $H_2$ in $CD_3CN$.

The formation of dimer 2 is also observed upon reaction of precatalyst 1 with hydrogen. FIG. 18 shows the dimer and cyclooctene formed from this reaction in CD₃CN solvent. Cyclooctene is slowly hydrogenated when the reaction mixture is allowed to sit at room temperature.

Observation of Intermediate 3 in Formic Acid

Figure 19A:
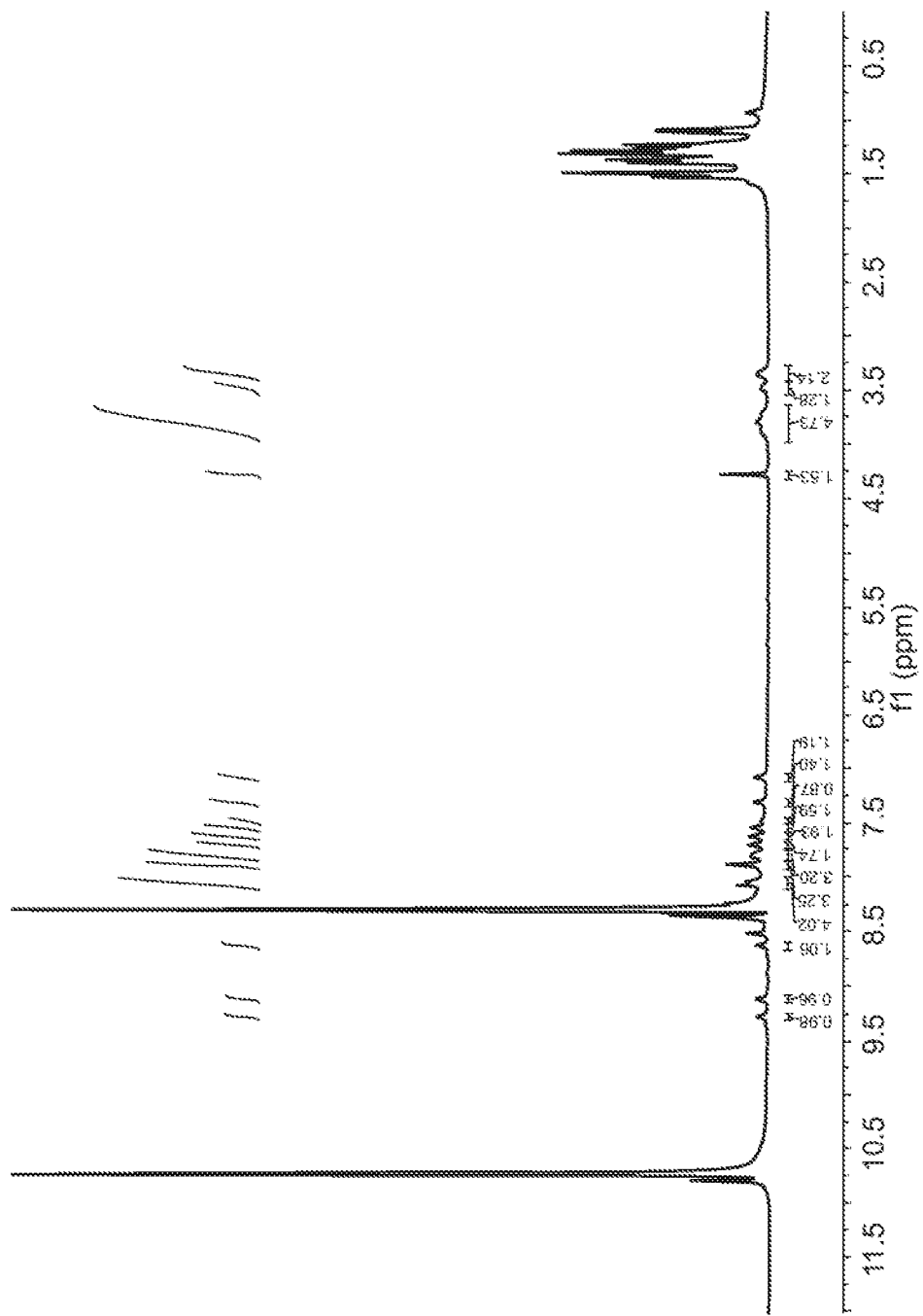
FIG. 19A provides a $^1H$ NMR spectrum of the iridium catalyst in formic acid. The bottom, hydride region, shows complexes 3a and 4.
Figure 19B:
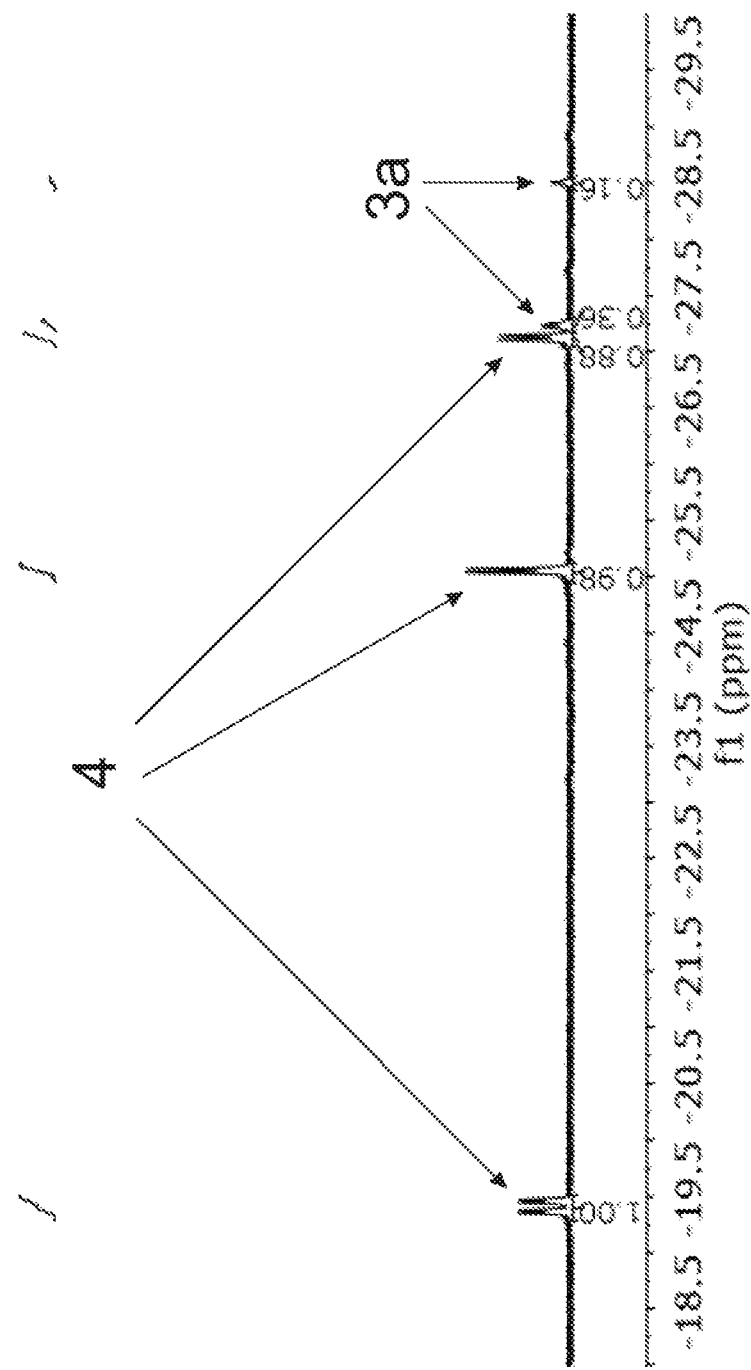
FIG. 19B provides a $^1H$ NMR spectrum of the iridium catalyst in formic acid. The bottom, hydride region, shows complexes 3a and 4.

We studied the catalyst resting state(s) in formic acid by dissolving, in the drybox, 10.0 mg of the iridium precatalyst and 10.0 mg of sodium formate in 1.0 mL of proteo formic acid in a J-Young tube. The J-Young tube was taken out of the drybox and was connected to a three-way valve, which was connected to a nitrogen line and a 50.0 mL gas buret. The tubings and the gas buret were purged with nitrogen for ca. 15 minutes. The plug valve and the three-way valve were opened such that gas produced go directly to the gas buret. The reaction flask was heated in an oil bath to 70° C. About 15 mL of gas was produced during heating. The solution was then allowed to cool to room temperature. The proteo formic acid solvent was evaporated under high vacuum and the resulting residue was left under high vacuum overnight. The residue was then dissolved in formic acid-d₂. The ¹H NMR spectrum of the residue is shown in FIG. 19. Examination of the hydride region reveals two resting states: (A) a minor resting state with two different hydrides at −27.24 and −28.51 ppm that integrate in a 2:1 ratio (consistent with the hydrides in the ¹H NMR of 3b, whose X⁻ ray structure is known). We formulate this species as dimer 3a. (B) The major resting state contains three different hydrides at −19.41, −25.05, and −27.13 ppm. We formulate this species as dimer 4 (see main text).

Complex 5

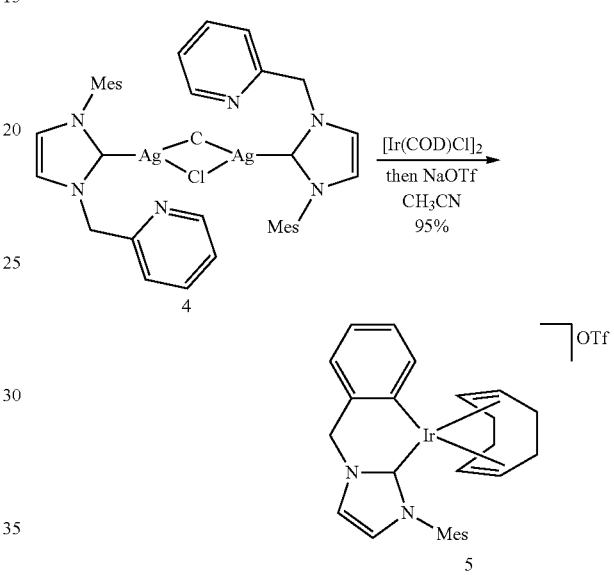

In the glovebox under nitrogen, in a 100 mL in a Schlenk flask, dichloro-di(1-(2,4,6-trimethylphenyl)-3-(2-picolyl)-imidazol-2-ylidene)-disilver(I) 4 (251 mg, 0.298 mmol) was added in small portions to a stirring solution of chloro(1,5-cyclooctadiene)Iridium(I) dimer (200.0 mg, 0.298 mmol) in 20 mL dry acetonitrile. After 30 minutes, sodium trifluoromethanesulfonate (102.5 mg, 0.596 mmol) was also added to the mixture. After stirring for another 30 minutes, the solution was filtered through a dry pad of celite to remove the sodium chloride byproduct. The solvent was evaporated under reduced pressure to yield a red glassy solid. This red solid was dissolved in 10 mL dry dichloromethane, and 20 mL dry hexanes was added to the solution to facilitate a precipitation. A red crystalline solid was acquired and dried under vacuum (400 mg, 93%). This sample was later determined to be spectroscopically pure under NMR. Slow recrystallization from dichloromethane and hexanes produced crystals suitable for X-ray crystallography. ¹H NMR ¹H NMR (600 MHz, methylene chloride-d₂) δ 8.50 (ddd, J=7.7, 1.6, 0.8 Hz, py 1H), 8.08 (ddd, J=7.8, 1.6, 0.7 Hz, py 1H), 8.01 (td, J=7.7, 1.5 Hz, py 1H), 7.70 (d, J=1.9 Hz, imi 1H), 7.48 (ddd, J=7.4, 5.6, 1.5 Hz, py 1H), 7.04 (s, mesityl-ar 1H), 7.00 (s, mesityl-ar 1H), 6.88 (d, J=1.9 Hz, imi 1H), 5.77 (s, methylene 1H), 5.74 (s, methylene 1H), 4.15 (s, COD sp² 1H), 4.07 (s, COD sp² 1H), 3.92 (s, COD sp² 1H), 3.21 (s, COD sp² 1H), 2.37 (s, mesityl-para-methyl 3H), 2.25-1.85 (m, COD sp³ 6H), 2.06 (s, mesityl-ortho-methyl 3H), 1.90 (s, mesityl-ortho-methyl 3H), 1.63 (s, COD sp³ 1H) 1.47 (s, COD sp³ 1H). ¹³C NMR (151 MHz, methylene chloride-$d_2$) δ 174.64, 153.38, 151.40, 140.51, 140.16, 135.32, 129.68, 129.46, 126.88, 126.74, 123.51, 122.54, 86.04, 82.80, 66.08, 64.43, 55.34, 34.99, 31.89, 31.44, 28.17, 21.23, 19.13, 17.94. $^{19}$F NMR (470 MHz, methylene chloride-$d_2$) δ-79.43. Elemental Analysis (CHNS) calc'd for $C_{27}H_{31}F_3IrN_3O_3S$: C, 44.62; H, 4.30; N, 5.78; S, 4.41. Found: C, 44.55; H, 4.24; N, 5.84; S, 4.24. IR (thin film/cm$^{-1}$) ν 3584, 3441, 2918, 2849, 2362, 1734, 1608, 1444, 1411, 1263, 1223, 1070, 1030, 853, 804, 636, 628. MS (MALDI) calc'd for $[C_{26}H_{31}IrN_3]$+578.2, found 577.9.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. An organometallic complex having formula B:

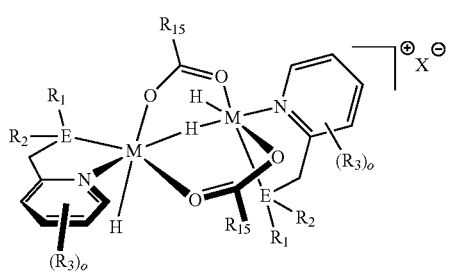

(B)

wherein:
M is a metal selected from the group consisting of beryllium, magnesium, aluminum, scandium, titanium, vanadium, chromium, manganese, iron, cobalt, nickel, copper, zinc, gallium, germanium, yttrium, zirconium, niobium, molybdenum, technetium, ruthenium, rhodium, palladium, silver, cadmium, indium, tin, antimony, lanthanum, cerium, praseodymium, neodymium, promethium, samarium, europium, gadolimium, terbium, dysprosium, holmium, erbium, thalium, ytterbium, lutetium, hafnium, tantalum, tungsten, rhenium, osmium, iridium, gold, platinum, thallium, lead, bismuth, polonium, thorium, protactinium, uranium, neptunium, and plutonium;
E is P, N, or C;
$R_1$, $R_2$ are each independently $C_{1-6}$ alkyl groups;
$R_3$ are each independently hydrogen, $C_{1-6}$ alkyl groups, $OR_{14}$, $NO_2$, or halogen;
o is 1, 2, 3, or 4;
$R_{14}$ is hydrogen or a $C_{1-6}$ alkyl group;
$R_{15}$ is hydrogen or a $C_{1-6}$ alkyl group; and
X$^-$ is a negatively charge counter ion.

2. The organometallic complex of claim 1 wherein M is a metal selected from the group consisting of ruthenium, rhodium, iridium, and iron.

3. The organometallic complex of claim 1 wherein M is iridium.

4. The organometallic complex of claim 1 wherein $R_1$, $R_2$ are each independently methyl, ethyl, butyl, n-propyl, isopropyl, n-butyl, sec-butyl, or t-butyl.

5. The organometallic complex of claim 1 wherein the $R_3$ is hydrogen.

6. The organometallic complex of claim 1 wherein $R_{15}$ is hydrogen, methyl, ethyl, butyl, n-propyl, isopropyl, n-butyl, sec-butyl, or t-butyl.

7. The organometallic complex of claim 1 wherein X$^-$ is halide or trifluoromethanesulfonate (OTf).

8. A method of dehydrogenating formic acid with an organometallic complex having formula B:

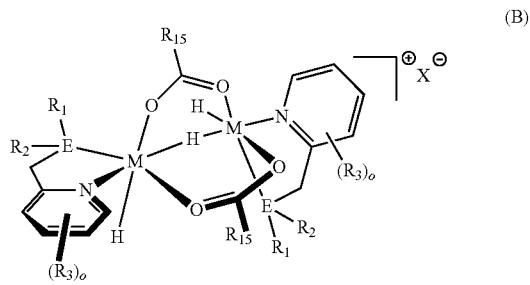

(B)

wherein:
M is a metal selected from the group consisting of beryllium, magnesium, aluminum, scandium, titanium, vanadium, chromium, manganese, iron, cobalt, nickel, copper, zinc, gallium, germanium, yttrium, zirconium, niobium, molybdenum, technetium, ruthenium, rhodium, palladium, silver, cadmium, indium, tin, antimony, lanthanum, cerium, praseodymium, neodymium, promethium, samarium, europium, gadolimium, terbium, dysprosium, holmium, erbium, thalium, ytterbium, lutetium, hafnium, tantalum, tungsten, rhenium, osmium, iridium, gold, platinum, thallium, lead, bismuth, polonium, thorium, protactinium, uranium, neptunium, and plutonium;
E is P, N, or C;
$R_1$, $R_2$ are each independently $C_{1-6}$ alkyl groups;
$R_3$ are each independently hydrogen, $C_{1-6}$ alkyl groups, $OR_{14}$, $NO_2$, or halogen;
o is 1, 2, 3, or 4;
$R_{14}$ is hydrogen or a $C_{1-6}$ alkyl group;
$R_{15}$ is hydrogen or a $C_{1-6}$ alkyl group; and
X$^-$ is a negatively charge counter ion, the method comprising:
a step of contacting the organometallic complex having formula B with formic acid in the presence of a base.

9. The method of claim 8 wherein the organometallic complex having formula B is contacted with formic acid under solvent free conditions.

10. The method of claim 8 wherein M is a metal selected from the group consisting of ruthenium, rhodium, iridium, and iron.

11. The method of claim 8 wherein M is iridium.

12. The method of claim 8 wherein $R_1$, $R_2$ are each independently methyl, ethyl, butyl, n-propyl, isopropyl, n-butyl, sec-butyl, or t-butyl.

13. The method of claim 8 wherein the $R_3$ is hydrogen.

14. The method of claim 8 wherein $R_{15}$ is hydrogen, methyl, ethyl, butyl, n-propyl, isopropyl, n-butyl, sec-butyl, or t-butyl.

15. The method of claim 8 wherein X$^-$ is halide or trifluoromethanesulfonate (OTf).

* * * * *